(12) United States Patent
Hastings et al.

(10) Patent No.: US 8,332,036 B2
(45) Date of Patent: Dec. 11, 2012

(54) LEADLESS CARDIAC STIMULATION SYSTEMS

(75) Inventors: Roger N. Hastings, Maple Grove, MN (US); William J. Drassler, Minnetonka, MN (US); Daniel M. Lafontaine, Plymouth, MN (US); Scott R. Smith, Chaska, MN (US); Anupama Sadasiva, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 870 days.

(21) Appl. No.: 11/683,584

(22) Filed: Mar. 8, 2007

(65) Prior Publication Data

US 2007/0150038 A1 Jun. 28, 2007

Related U.S. Application Data

(62) Division of application No. 10/971,550, filed on Oct. 20, 2004, now Pat. No. 7,532,933.

(51) Int. Cl.
  *A61N 1/05* (2006.01)
  *A61N 1/37* (2006.01)
  *A61N 1/08* (2006.01)
(52) U.S. Cl. ............... 607/32; 607/60; 607/61
(58) Field of Classification Search .......... 607/30, 607/32, 33, 60, 61
  See application file for complete search history.

(56) References Cited

U.S. PATENT DOCUMENTS

| 3,057,356 A | 9/1962 | Greatbatch | 128/422 |
| 3,357,434 A | 12/1967 | Abell | 128/419 |
| 3,596,662 A | 8/1971 | Bolduc | |
| 3,667,477 A | 6/1972 | Susset et al. | 128/419 E |
| 3,713,449 A | 1/1973 | Mulier | |
| 3,727,616 A | 4/1973 | Lenzkes | 128/422 |
| 3,835,864 A | 9/1974 | Rasor et al. | |
| 3,902,501 A | 9/1975 | Citron et al. | |
| 3,942,535 A | 3/1976 | Schulman | |
| 3,943,936 A | 3/1976 | Rasor et al. | |
| 4,157,720 A | 6/1979 | Greatbatch | |
| 4,162,679 A | 7/1979 | Reenstierna | |

(Continued)

FOREIGN PATENT DOCUMENTS

EP  0758542 A1  2/1997

(Continued)

OTHER PUBLICATIONS

"Energy management, wireless and system solutions for highly integrated implantable devices" Doctoral Thesis by Jordi Parramon I Piella for the Universitat Autonoma de Barcelona, certified Dec. 2001.

(Continued)

*Primary Examiner* — Tammie K Heller
(74) *Attorney, Agent, or Firm* — Schwegman Lundberg & Woessner, P.A.

(57) ABSTRACT

Various configurations of systems that employ leadless electrodes to provide pacing therapy are provided. In one example, a system that provides multiple sites for pacing of myocardium of a heart includes wireless pacing electrodes that are implantable at sites proximate the myocardium using a percutaneous, transluminal, catheter delivery system. Each of the electrodes contains a source of electrical energy for pacing the myocardium and is adapted to receive electromagnetic energy from a source outside the myocardium. The system also includes a source adapted for placement outside the myocardium and that uses locally measured electrocardiograms to synchronize pacing of the heart by sending electromagnetic commands to the electrodes to pace the myocardium surrounding the electrodes. Also disclosed is various configurations of such systems, wireless electrode assemblies, and delivery catheters for delivering and implanting the electrode assemblies.

13 Claims, 15 Drawing Sheets

U.S. PATENT DOCUMENTS

| | | |
|---|---|---|
| 4,198,991 A | 4/1980 | Harris |
| 4,256,115 A | 3/1981 | Bilitch |
| 4,441,210 A | 4/1984 | Hochmair et al. |
| 4,641,664 A | 2/1987 | Botvidsson |
| 4,644,957 A | 2/1987 | Ricciardelli et al. |
| 4,681,111 A | 7/1987 | Silvian |
| 4,721,118 A | 1/1988 | Harris |
| 4,830,006 A | 5/1989 | Haluska et al. ......... 128/419 PG |
| 4,858,623 A | 8/1989 | Bradshaw et al. |
| 4,860,750 A | 8/1989 | Frey et al. |
| 4,953,564 A | 9/1990 | Berthelsen |
| 4,987,897 A | 1/1991 | Funke ..................... 128/419 PG |
| 5,139,033 A | 8/1992 | Everett et al. |
| 5,143,090 A | 9/1992 | Dutcher et al. |
| 5,178,149 A | 1/1993 | Imburgia et al. ......... 128/662.06 |
| 5,193,539 A | 3/1993 | Schulman et al. ........ 128/419 R |
| 5,193,540 A | 3/1993 | Schulman et al. |
| 5,234,437 A | 8/1993 | Sepetka |
| 5,246,014 A | 9/1993 | Williams et al. |
| 5,250,071 A | 10/1993 | Palermo |
| 5,255,693 A | 10/1993 | Dutcher et al. |
| 5,261,916 A | 11/1993 | Engelson |
| 5,300,107 A | 4/1994 | Stokes et al. |
| 5,304,195 A | 4/1994 | Twyford, Jr. et al. |
| 5,312,415 A | 5/1994 | Palermo |
| 5,312,439 A | 5/1994 | Loeb |
| 5,324,316 A | 6/1994 | Schulman et al. |
| 5,324,325 A | 6/1994 | Moaddeb |
| 5,336,252 A | 8/1994 | Cohen |
| 5,350,397 A | 9/1994 | Palermo et al. |
| 5,383,924 A | 1/1995 | Brehier |
| 5,405,367 A | 4/1995 | Schulman et al. |
| 5,411,535 A | 5/1995 | Fujii et al. |
| 5,411,537 A | 5/1995 | Munshi et al. .................. 607/33 |
| 5,447,533 A | 9/1995 | Vachon et al. |
| 5,487,760 A | 1/1996 | Villafana |
| 5,531,780 A | 7/1996 | Vachon |
| 5,571,148 A | 11/1996 | Loeb et al. ....................... 607/57 |
| 5,622,168 A | 4/1997 | Keusch et al. |
| 5,735,887 A | 4/1998 | Barreras, Sr. et al. |
| 5,755,764 A | 5/1998 | Schroeppel |
| 5,772,693 A | 6/1998 | Brownlee |
| 5,779,715 A | 7/1998 | Tu |
| 5,800,535 A | 9/1998 | Howard, III ..................... 623/10 |
| 5,814,089 A | 9/1998 | Stokes et al. |
| 5,833,715 A | 11/1998 | Vachon et al. |
| 5,851,227 A | 12/1998 | Spehr |
| 5,871,532 A | 2/1999 | Schroeppel |
| 6,035,239 A | 3/2000 | Patag et al. |
| 6,123,724 A | 9/2000 | Denker |
| 6,132,456 A | 10/2000 | Sommer et al. |
| 6,141,588 A | 10/2000 | Cox et al. ........................... 607/9 |
| 6,144,880 A | 11/2000 | Ding et al. |
| 6,164,284 A | 12/2000 | Schulman et al. |
| 6,200,303 B1 | 3/2001 | Verrior et al. |
| 6,208,894 B1 | 3/2001 | Schulman et al. |
| 6,223,079 B1 | 4/2001 | Bakels et al. |
| 6,240,316 B1 | 5/2001 | Richmond et al. |
| 6,266,567 B1 | 7/2001 | Ishikawa et al. |
| 6,315,721 B2 | 11/2001 | Schulman et al. |
| 6,345,202 B2 | 2/2002 | Richmond et al. |
| 6,351,673 B1 | 2/2002 | Ding et al. |
| 6,360,127 B1 | 3/2002 | Ding et al. |
| 6,363,938 B2 | 4/2002 | Saadat et al. |
| 6,370,434 B1 | 4/2002 | Zhang et al. |
| 6,381,495 B1 | 4/2002 | Jenkins |
| 6,385,472 B1 | 5/2002 | Hall et al. |
| 6,409,674 B1 | 6/2002 | Brockway et al. |
| 6,445,953 B1 | 9/2002 | Bulkes et al. .................... 607/33 |
| 6,456,256 B1 | 9/2002 | Amundson et al. ........... 343/873 |
| 6,501,983 B1 | 12/2002 | Natarajan et al. |
| 6,542,775 B2 | 4/2003 | Ding et al. |
| 6,556,874 B2 | 4/2003 | Audoglio |
| 6,564,807 B1 | 5/2003 | Schulman et al. |
| 6,582,441 B1 | 6/2003 | He et al. |
| 6,589,230 B2 | 7/2003 | Gia et al. |
| 6,647,291 B1 | 11/2003 | Bonner et al. ...................... 607/5 |
| 6,647,292 B1 | 11/2003 | Bardy et al. |
| 6,783,499 B2 | 8/2004 | Schwartz |
| 6,856,836 B2 | 2/2005 | Ding et al. |
| 6,859,665 B2 | 2/2005 | Ding et al. |
| 6,895,280 B2 | 5/2005 | Meadows et al. |
| 6,907,285 B2 | 6/2005 | Denker et al. |
| 6,917,833 B2 | 7/2005 | Denker et al. |
| 7,003,350 B2 | 2/2006 | Denker et al. |
| 7,006,864 B2 | 2/2006 | Echt et al. |
| 7,050,849 B2 | 5/2006 | Echt et al. |
| 7,076,305 B2 | 7/2006 | Imran et al. |
| 7,184,830 B2 | 2/2007 | Echt et al. |
| 7,209,783 B2 | 4/2007 | Fellows et al. |
| 7,231,260 B2 | 6/2007 | Wallace et al. |
| 7,410,497 B2 | 8/2008 | Hastings et al. |
| 7,522,962 B1 | 4/2009 | Doron et al. |
| 7,532,932 B2 | 5/2009 | Denker et al. |
| 7,532,933 B2 | 5/2009 | Hastings et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,615,010 B1 | 11/2009 | Najafi et al. |
| 7,647,109 B2 | 1/2010 | Hastings et al. |
| 7,650,186 B2 | 1/2010 | Hastings et al. |
| 7,702,392 B2 | 4/2010 | Echt et al. |
| 7,765,001 B2 | 7/2010 | Echt et al. |
| 7,809,438 B2 | 10/2010 | Echt et al. |
| 7,840,281 B2 | 11/2010 | Kveen et al. |
| 7,848,815 B2 | 12/2010 | Brisken et al. |
| 7,848,823 B2 | 12/2010 | Drasler et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,541 B2 | 3/2011 | Cowan et al. |
| 7,899,542 B2 | 3/2011 | Cowan et al. |
| 7,937,161 B2 | 5/2011 | Hastings et al. |
| 7,996,087 B2 | 8/2011 | Cowan et al. |
| 8,050,774 B2 | 11/2011 | Kveen et al. |
| 8,185,213 B2 | 5/2012 | Kveen et al. |
| 8,204,605 B2 | 6/2012 | Hastings et al. |
| 2001/0018547 A1 | 8/2001 | Mechlenburg et al. ......... 600/15 |
| 2002/0052632 A1 | 5/2002 | Ben-Haim et al. |
| 2002/0065543 A1 | 5/2002 | Gomperz et al. |
| 2002/0077556 A1 | 6/2002 | Schwartz |
| 2002/0077685 A1 | 6/2002 | Sundquist et al. |
| 2002/0123774 A1 | 9/2002 | Loeb et al. |
| 2002/0123785 A1 | 9/2002 | Zhang et al. |
| 2002/0138009 A1 | 9/2002 | Brockway et al. |
| 2002/0183791 A1 | 12/2002 | Denker et al. ...................... 607/5 |
| 2002/0198604 A1 | 12/2002 | Schulman et al. |
| 2003/0036773 A1 | 2/2003 | Whitehurst et al. |
| 2003/0050681 A1 | 3/2003 | Pianca et al. |
| 2003/0088278 A1 | 5/2003 | Bardy |
| 2003/0109914 A1 | 6/2003 | Westlund et al. |
| 2003/0158584 A1 | 8/2003 | Cates et al. |
| 2003/0181958 A1 | 9/2003 | Dobak, III ...................... 607/58 |
| 2003/0181959 A1 | 9/2003 | Dobak, III ...................... 607/58 |
| 2004/0059392 A1 | 3/2004 | Parramon et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0147973 A1 | 7/2004 | Hauser et al. |
| 2004/0176822 A1 | 9/2004 | Thompson et al. |
| 2005/0021108 A1 | 1/2005 | Klosterman et al. |
| 2005/0025797 A1 | 2/2005 | Wang et al. |
| 2005/0057905 A1 | 3/2005 | He et al. |
| 2005/0096702 A1 | 5/2005 | Denker et al. |
| 2005/0131511 A1 | 6/2005 | Westlund |
| 2005/0182456 A1 | 8/2005 | Ziobro et al. |
| 2005/0182465 A1 | 8/2005 | Ness |
| 2005/0251238 A1 | 11/2005 | Wallace et al. |
| 2005/0251240 A1 | 11/2005 | Doan |
| 2005/0261741 A1 | 11/2005 | Libbus et al. |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0085039 A1 | 4/2006 | Hastings et al. |
| 2006/0085041 A1 | 4/2006 | Hastings et al. |

| | | | |
|---|---|---|---|
| 2006/0085042 A1 | 4/2006 | Hastings et al. | |
| 2006/0136001 A1 | 6/2006 | Ortega et al. | |
| 2006/0173504 A1 | 8/2006 | Zhu et al. | |
| 2006/0173505 A1 | 8/2006 | Salo et al. | |
| 2006/0178719 A1 | 8/2006 | Ideker et al. | |
| 2006/0206170 A1 | 9/2006 | Denker et al. | |
| 2007/0075905 A1 | 4/2007 | Denker et al. | |
| 2007/0106357 A1 | 5/2007 | Denker et al. | |
| 2007/0135882 A1 | 6/2007 | Drasler et al. | |
| 2007/0135883 A1 | 6/2007 | Drasler et al. | |
| 2007/0150009 A1 | 6/2007 | Kveen et al. | |
| 2007/0150037 A1 | 6/2007 | Hastings et al. | |
| 2007/0150038 A1 | 6/2007 | Hastings et al. | |
| 2007/0203556 A1 | 8/2007 | Rutten et al. | |
| 2007/0219590 A1 | 9/2007 | Hastings et al. | |
| 2007/0239248 A1 | 10/2007 | Hastings et al. | |
| 2008/0039904 A1 | 2/2008 | Bulkes et al. | |
| 2008/0046040 A1 | 2/2008 | Denker et al. | |
| 2008/0077184 A1 | 3/2008 | Denker et al. | |
| 2008/0077188 A1 | 3/2008 | Denker et al. | |
| 2008/0109054 A1 | 5/2008 | Hastings et al. | |
| 2008/0319502 A1 | 12/2008 | Sunagawa et al. | |
| 2009/0018599 A1 | 1/2009 | Hastings et al. | |
| 2009/0204170 A1 | 8/2009 | Hastings et al. | |
| 2009/0234407 A1 | 9/2009 | Hastings et al. | |
| 2010/0100144 A1 | 4/2010 | Shuros et al. | |
| 2011/0034939 A1 | 2/2011 | Kveen et al. | |
| 2011/0213233 A1 | 9/2011 | Stevenson et al. | |

FOREIGN PATENT DOCUMENTS

| | | |
|---|---|---|
| EP | 1 166 820 | 1/2002 |
| EP | 1166832 A1 | 1/2002 |
| EP | 1264572 A1 | 12/2002 |
| EP | 1809372 A1 | 7/2007 |
| EP | 1812104 A1 | 8/2007 |
| EP | 1835962 A1 | 9/2007 |
| JP | 61-203730 A | 9/1986 |
| JP | 62-254770 A | 6/1987 |
| JP | 02-307481 A | 12/1990 |
| JP | 05-076501 | 3/1993 |
| JP | 05-245215 A | 9/1993 |
| JP | 06-510459 A | 11/1994 |
| JP | 07-016299 A | 1/1995 |
| JP | 09-508054 A | 8/1997 |
| JP | 10-509901 A | 9/1998 |
| JP | 2000-502931 A | 3/2000 |
| JP | 2001-511406 A | 8/2001 |
| JP | 2002-510222 A | 4/2002 |
| JP | 2002-514478 A | 5/2002 |
| JP | 2004-173790 A | 6/2004 |
| NZ | 526115 | 10/2006 |
| NZ | 539770 | 10/2007 |
| NZ | 539771 | 10/2007 |
| WO | WO-95/10226 A1 | 4/1995 |
| WO | WO-96/20754 A1 | 7/1996 |
| WO | WO-97/25098 A1 | 7/1997 |
| WO | WO-98/26840 A1 | 6/1998 |
| WO | WO 99/06102 | 2/1999 |
| WO | WO-99/06102 A1 | 2/1999 |
| WO | WO-99/58191 A1 | 11/1999 |
| WO | WO-99/64104 A1 | 12/1999 |
| WO | WO-00/30534 A1 | 6/2000 |
| WO | WO-01/00114 A1 | 1/2001 |
| WO | WO-03/041793 A2 | 5/2003 |
| WO | WO 03/053491 | 7/2003 |
| WO | WO-03/053491 A2 | 7/2003 |
| WO | WO-03/076010 A2 | 9/2003 |
| WO | WO-2004/002572 A1 | 1/2004 |
| WO | WO-2004/012811 A1 | 2/2004 |
| WO | WO-2006/045073 A1 | 4/2006 |
| WO | WO-2006/045074 A2 | 4/2006 |
| WO | WO 2006/045075 | 4/2006 |
| WO | WO-2006/096685 A1 | 9/2006 |
| WO | WO-2007/067231 A1 | 6/2007 |
| WO | WO-2007/067253 A1 | 6/2007 |
| WO | WO-2007/115044 A2 | 10/2007 |
| WO | WO-2008/034005 A2 | 3/2008 |

OTHER PUBLICATIONS

"Breakthrough Products Could Put Lesser-Known Firms on the Map", by E. Swain, *MDEA 2004*, pp. 56-58, Apr. 2004.

"Novel Passive Implantable Atrial Defibrillator Using Transcutaneous Radiofrequency Energy Transmission Successfully Cardioverts Atrial Fibrillation" by Manoharan et al., for *Circulation*, pp. 1382-1388, Sep. 16, 2003.

Wagner, "Electrodes, Leads, and Biocompatibility," *Design of Cardiac Pacemakers*, 1993, Chapter 6, pp. 133-160 and TOC.

"U.S. Appl. No. 10/971,550, Notice of Allowance mailed Jul. 14, 2008", 4 pgs.

"U.S. Appl. No. 10/971,550, Response filed Feb. 22, 2007 to Restriction Requirement mailed Jan. 22, 2007", 1 pg.

"U.S. Appl. No. 10/971,550, Restriction Requirement mailed Jan. 22, 2007", 22 pgs.

"U.S. Appl. No. 10/971,550, Notice of Allowance mailed Dec. 22, 2008", 4 pgs.

"U.S. Appl. No. 10/971,550, Non-Final Office Action mailed Mar. 19, 2007", 11 pgs.

"U.S. Appl. No. 10/971,550, Non-Final Office Action mailed Nov. 5, 2007", 19 pgs.

"U.S. Appl. No. 10/971,550, Response Filed Sep. 4, 2007 to Non-Final Office Action mailed Mar. 19, 2007", 15 pgs.

"U.S. Appl. No. 10/971,550, Response filed Mar. 25, 2008 to Non-Final Office Action mailed Nov. 5, 2007", 17 pgs.

"U.S. Appl. No. 11,075,375, Response filed May 7, 2007 to Restriction Requirement mailed Apr. 10, 2007", 8 pgs.

"U.S. Appl. No. 11,075,375, Restriction Requirement mailed Apr. 10, 2007", 6 pgs.

"U.S. Appl. No. 11,075,375, Response filed May 22, 2008 to Final Office Action mailed Jan. 23, 2008", 16 pgs.

"U.S. Appl. No. 11/075,375, Non-Final Office Action mailed Jun. 8, 2007", 11 pgs.

"U.S. Appl. No. 11/075,375, Response filed Oct. 26, 2007 to Non-Final Office Action mailed Jun. 8, 2007", 10 pgs.

"U.S. Appl. No. 11/075,375, Final Office Action mailed Jan. 23, 2008", 10 pgs.

"U.S. Appl. No. 11/075,375 ,Final Office Action mailed Apr. 16, 2009", 10 pgs.

"U.S. Appl. No. 11/075,375, Amendment and Response filed Jan. 12, 2009 to Non-Final Office Action mailed Aug. 11, 2008", 18 pgs.

"U.S. Appl. No. 11/075,375, Non-Final Office Action mailed Aug. 11, 2008", 15 pgs.

"U.S. Appl. No. 11/075,376, Restriction Requirement mailed Apr. 10, 2007", 6 pgs.

"U.S. Appl. No. 11/075,376, Non-Final Office Action mailed Aug. 20, 2008", 15 pgs.

"U.S. Appl. No. 11/075,376, Final Office Action mailed Jan. 7, 2008", 11 pgs.

"U.S. Appl. No. 11/075,376, Non-Final Office Action mailed Jun. 26, 2007", 9 pgs.

"U.S. Appl. No. 11/075,376, Response filed May 7, 2007 to Restriction Requirement mailed Apr. 10, 2007", 10 pgs.

"U.S. Appl. No. 11/075,376, Response filed Oct. 26, 2007 to Non-Final Office Action mailed Jun. 26, 2007", 14 pgs.

"U.S. Appl. No. 11/075,376, Response filed Jan. 21, 2009 to Non-Final Office Action mailed Aug. 20, 2008", 22 pgs.

"U.S. Appl. No. 11/075,376, Response filed Jun. 9, 2008 to Final Office Action mailed Jan. 7, 2008", 20 pgs.

"U.S. Appl. No. 11/075,376, Final Office Action mailed Apr. 8, 2009", 17 pgs.

"U.S. Appl. No. 11/075,376, Response filed Jul. 8, 2009 to Final Office Action mailed Apr. 8, 2009", 11 pgs.

"U.S. Appl. No. 11/394,601, Response filed May 4, 2009 to Restriction Requirement mailed Apr. 2, 2009", 9 pgs.

"U.S. Appl. No. 11/394,601, Restriction Requirement mailed Apr. 2, 2009", 10 pgs.

"U.S. Appl. No. 11/549,352, Non-Final Office Action mailed Feb. 5, 2008", 10 pgs.

"U.S. Appl. No. 11/549,352, Response filed Jul. 7, 2008 to Non-Final Office Action mailed Feb. 5, 2008", 17 pgs.

"U.S. Appl. No. 11/549,352, Final Office Action mailed Mar. 9, 2009", 10 pgs.

"U.S. Appl. No. 11/549,352, Notice of Panel Decision from Pre-Appeal Brief Review mailed Feb. 2, 2009", 2 pgs.

"U.S. Appl. No. 11/549,352, Pre-Appeal Brief for Review filed Dec. 20, 2008", 5 pgs.

"U.S. Appl. No. 11/549,352, Final Office Action mailed on Aug. 26, 2008", 14 pgs.

"U.S. Appl. No. 11/683,577, Non Final Office Action mailed Mar. 5, 2009", 13 pgs.

"U.S. Appl. No. 11/745,070, Non Final Office Action mailed Apr. 27, 2009", 11 pgs.

"European Application Serial No. 06825988.6, Office Action mailed Mar. 4, 2009", 7 pgs.

"European Application Serial No. 07759589.0, Office Action mailed Jan. 29, 2009", 3 pgs.

"International Application Serial No. PCT/US2005/037978, International Search Report mailed Jun. 13, 2006", 5 pgs.

"International Application Serial No. PCT/US2005/037978, Written Opinion mailed Jun. 13, 2006", 12 pgs.

"International Application Serial No. PCT/US2006/040291, International Search Report mailed Apr. 4, 2007", 5 pgs.

"International Application Serial No. PCT/US2006/040291 Written Opinion mailed Apr. 4, 2007", 9 pgs.

"International Application Serial No. PCT/US2005/037979, International Search Report mailed Mar. 21, 2006", 4 pgs.

"International Application Serial No. PCT/US2005/037979, Written Opinion mailed Mar. 21, 2006", 8 pgs.

"International Application Serial No. PCT/US2007/078405, International Search Report mailed May 20, 2008", 5 pgs.

"International Application Serial No. PCT/US2007/078405, Written Opinion mailed May 20, 2007", 7 pgs.

"International Application Serial No. PCT/US2009/000693, International Search Report mailed May 8, 2009", 5 pgs.

"International Application Serial No. PCT/US2009/000693, Written Opinion mailed May 8, 2009", 8 pgs.

"Telemetry Research Transcutaneous Energy Transfer (TET) Technology Summary", *Telemet Research Ltd.*, www.telemetryresearch.com, (No date listed), 1 pg.

Busch, M., et al., "On the Heating of Inductively Coupled Resonators (Stents) During MRI Examinations", *Magnetic Resonance in Medicine*, 54, (2005), 775-785.

Si, P., et al., "A Frequency Control Method for Regulating Wireless Power to Implantable Devices", *IEEE Transactions on Biomedical Circuits and Systems*, 2(1), (Mar. 2008), 22-29.

"U.S. Appl. No. 11/683,577 Final Office Action Mailed Nov. 9, 2009", 19 pgs.

"U.S. Appl. No. 10/971,550, Amendment Under 37 C.F.R. Sec. 1.312 filed Mar. 20, 2009", 6 pgs.

"U.S. Appl. No. 11/075,375, Response filed Jul. 16, 2009 to Final Office Action mailed Apr. 16, 2009", 13 pgs.

"U.S. Appl. No. 11/075,376, Notice of Allowance mailed Aug. 24, 2009", 6 pgs.

"U.S. Appl. No. 11/316,120, Response filed Jul. 17, 2009 to Non Final Office Action mailed Apr. 17, 2009", 13 pgs.

"U.S. Appl. No. 11/394,601, Non-Final Office Action mailed Sep. 2, 2009", 6 pgs.

"U.S. Appl. No. 11/490,576, Non-Final Office Action mailed Oct. 5, 2009", 8 pgs.

"U.S. Appl. No. 11/490,916, Response filed Sep. 3, 2009 to Non Final Office Action mailed May 5, 2009", 13 pgs.

"U.S. Appl. No. 11/511,152, Final Office Action mailed Aug. 10, 2009", 13 pgs.

"U.S. Appl. No. 11/683,577, Response filed Aug. 5, 2009 to Non Final Office Action mailed Mar. 5, 2009", 10 pgs.

"U.S. Appl. No. 11/745,070, Response filed Jul. 27, 2009 to Non Final Office Action mailed Apr. 27, 2009", 11 pgs.

"U.S. Appl. No. 11/745,105, Non-Final Office Action mailed Sep. 18, 2009", 9 pgs.

"U.S. Appl. No. 11/549,352, Appeal Brief filed Sep. 9, 2009", 37 pgs.

"European Application Serial No. 07759589.0, Response filed Jun. 5, 2009 to Office Action mailed Jan. 29, 2009", 6 pgs.

"U.S. Appl. No. 10/971,550, PTO Response to 312 Amendment mailed Apr. 6, 2009", 2 pgs.

"U.S. Appl. No. 11/316,120, Supplemental Notice of Allowance mailed Sep. 1, 2011", 4 pgs.

"U.S. Appl. No. 11/490,576, Decision on Pre-Appeal Brief Request mailed Aug. 30, 2011", 2 pgs.

"U.S. Appl. No. 11/745,105, Response filed Sep. 12, 2011 to Non-Final Office Action mailed May 11, 2011", 13 pgs.

"U.S. Appl. No. 12/361,884, Supplemental Preliminary Amendment filed Jul. 27, 2011", 12 pgs.

"U.S. Appl. No. 12/365,428, Non Final Office Action mailed Aug. 31, 2011", 9 pgs.

"Japanese Application Serial No. 2007-538088, Response filed Aug. 25, 2011 to Office Action dated Jun. 13, 2011", (w/ English Translation of Amended Claims), 9 pgs.

"U.S. Appl. No. 11/316,120, Non-Final Office Action mailed May 27, 2010", 8 pgs.

"U.S. Appl. No. 11/316,120, Response filed Apr. 12, 2010 to Final Office Action mailed Nov. 12, 2009", 12 pgs.

"U.S. Appl. No. 11/394,601, Final Office Action mailed Mar. 22, 2010", 7 pgs.

"U.S. Appl. No. 11/394,601, Response filed Dec. 2, 2009 to Non Final Office Action mailed Sep. 2, 2009", 11 pgs.

"U.S. Appl. No. 11/490,576, Non-Final Office Action mailed Jul. 12, 2010", 9 pgs.

"U.S. Appl. No. 11/490,576, Response filed Mar. 5, 2010 to Non Final Office Action mailed Oct. 5, 2009", 13 pgs.

"U.S. Appl. No. 11/490,916, Final Office Action mailed Dec. 17, 2009", 11 pgs.

"U.S. Appl. No. 11/490,916, Notice of Allowance mailed Jul. 9, 2010", 4 pgs.

"U.S. Appl. No. 11/490,916, Response filed Apr. 15, 2010 to Final Office Action mailed Dec. 17, 2009", 12 pgs.

"U.S. Appl. No. 11/511,152, Non-Final Office Action mailed Dec. 30, 2009", 13 pgs.

"U.S. Appl. No. 11/511,152, Response filed Jun. 30, 2010 to Non-Final Office Action mailed Dec. 30, 2009", 12 pgs.

"U.S. Appl. No. 11/683,577, Response filed May 7, 2010 to Final Office Action mailed Nov. 9, 2009", 14 pgs.

"U.S. Appl. No. 11/745,070, Final Office Action mailed Dec. 11, 2009", 18 pgs.

"U.S. Appl. No. 11/745,105, Final Office Action mailed Mar. 30, 2010", 9 pgs.

"U.S. Appl. No. 11/745,105, Response filed Jan. 19, 2010 to Non Final Office Action mailed Sep. 18, 2009", 12 pgs.

"U.S. Appl. No. 11/745,105, Response filed Jun. 22, 2009 to Restriction Requirement mailed May 21, 2009", 6 pgs.

"U.S. Appl. No. 11/745,105, Restriction Requirement mailed May 21, 2009", 6 pgs.

"European Application Serial No. 05815206.7, Communication Dec. 18, 2009", 4 pgs.

"European Application Serial No. 05815215.8, Communication mailed Dec. 18, 2009", 2 pgs.

"European Application Serial No. 05817448.3, Communication mailed Dec. 18, 2009", 2 pgs.

"European Application Serial No. 07759589.0, Office Action Mailed Feb. 18, 2010", 3 pgs.

"European Application Serial No. 07759589.0, Office Action Response filed Jun. 24, 2010", 6 pgs.

"U.S. Appl. No. 11/490,576, Response filed Apr. 9, 2012 to Non Final Office Action mailed Nov. 9, 2011", 11 pgs.

"U.S. Appl. No. 11/490,576, Non Final Office Action mailed Nov. 9, 2011", 8 pgs.

"U.S. Appl. No. 11/490,576, Notice of Allowance mailed Jun. 4, 2012", 8 pgs.

"U.S. Appl. No. 11/745,105, Non Final Office Action mailed Feb. 7, 2012", 12 pgs.

"U.S. Appl. No. 11/745,105, Notice of Allowance mailed Oct. 31, 2011", 5 pgs

"U.S. Appl. No. 12/361,884, Final Office Action mailed Jul. 3, 2012", 17 pgs.

"U.S. Appl. No. 12/361,884, Non Final Office Action mailed Oct. 12, 2011", 15 pgs.

"U.S. Appl. No. 12/361,884, Response filed Apr. 12, 2012 to Non Final Action mailed Oct. 12, 2011", 21 pgs.
"U.S. Appl. No. 12/365,428, Notice of Allowance mailed Feb. 22, 2012", 7 pgs.
"U.S. Appl. No. 12/365,428, Response filed 01-30112 to Non Final Office Action mailed Aug. 31, 2011 ", 15 pgs.
"U.S. Appl. No. 12/910,106, Notice of Allowance mailed Jan. 26, 2012", 6 pgs.
"U.S. Appl. No. 12/910,106, Notice of Allowance mailed Oct. 27, 2011", 5 pgs.
"U.S. Appl. No. 11/549,352, Appeal Decision mailed Jul. 17, 2012", 9 pgs.
"European Application Serial No. 05815206.7, Office Action mailed May 16, 2012", 5 pgs.
"European Application Serial No. 05817448.3, Office Action mailed May 16, 2012", 5 pgs.
"European Application Serial No. 07759589.0, Written Submission filed Dec. 5, 2011 to Summons to Attend Oral Proceedings dated May 17, 2011", 16 pgs.
"Japanese Application Serial No. 2007-538087, Office Action mailed Apr. 17, 2012", (w/ English Translation), 8 pgs.
"Japanese Application Serial No. 2007-538087, Office Action mailed Oct. 5, 2011", (w/ English Translation), 14 pgs.
"Japanese Application Serial No. 2007-538087, Response filed Mar. 23, 2012 to Office Action mailed Oct. 5, 2011", (w/ English Translation of Claims), 9 pgs.
"Japanese Application Serial No. 2007-538087, Response filed Jul. 13, 2012 to Office Action mailed Apr. 17, 2012", (w/ English Translation of Amended Claims), 13 pgs.
"Japanese Application Serial No. 2007-538088, Notice of Final Rejection mailed Dec. 6, 2011", (w/ English Translation), 9 pgs.
"Japanese Application Serial No. 2007-538088, Response filed Mar. 27, 2012 to Final Office Action mailed Dec. 6, 2011", (w/ English Translation of Claims), 11 pgs.
"Japanese Application Serial No. 2008-544324, Office Action mailed May 22, 2012", (w/ English Translation), 5 pgs.
"Japanese Application Serial No. 2008-544324, Office Action mailed Nov. 22, 2011", (w/ English Translation), 5 pgs.
"Japanese Application Serial No. 2008-544324, Response filed Jan. 27, 2012", (w/ English Translation of Amended Claims), 10 pgs.
"Japanese Application Serial No. 2008-544332, Office Action mailed Nov. 29, 2011", (in/ English Translation), 5 pgs.
"Japanese Application Serial No. 2008-544332, Response filed Mar. 19, 2012 to Office Action mailed Nov. 29, 2011", (w/ English Translation of Claims), 9 pgs.
"Japanese Application Serial No. 2009-503252, Office Action mailed Mar. 21, 2012", (w/ English Translation), 9 pgs.
"Japanese Application Serial No. 2009-503252, Response filed Jun. 20, 2012 to Office Action mailed Mar. 21, 2012", (w/ English Claims), 9 pgs.
"U.S. Appl. No. 10/971,550, Examiner Interview Summary mailed Jan. 22, 2008", 4 pgs.
"U.S. Appl. No. 11/075,375, Examiner Interview Summary mailed Jan. 12, 2009", 4 pgs.
"U.S. Appl. No. 11/075,375, Examiner Interview Summary mailed May 1, 2008", 4 pgs.
"U.S. Appl. No. 11/075,375, Notice of Allowance mailed Sep. 4, 2009", 6 pgs.
"U.S. Appl. No. 11/075,376, Examiner Interview Summary mailed Jan. 12, 2009", 4 pgs.
"U.S. Appl. No. 11/075,376, Examiner Interview Summary mailed Apr. 2, 2008", 4 pgs.
"U.S. Appl. No. 11/316,120, Decision on Pre-Appeal Brief Request mailed Apr. 19, 2011", 2 pgs.
"U.S. Appl. No. 11/316,120, Final Office Action mailed Oct. 28, 2010", 8 pgs.
"U.S. Appl. No. 11/316,120, Non Final Office Action mailed Apr. 11, 2008", 7 pgs.
"U.S. Appl. No. 11/316,120, Notice of Allowance mailed Jul. 20, 2011", 7 pgs.
"U.S. Appl. No. 11/316,120, Pre-Appeal Brief Request filed Mar. 25, 2011", 5 pgs.
"U.S. Appl. No. 11/316,120, Response filed Mar. 25, 2011 to Final Office Action mailed Oct. 28, 2010", 8 pgs.
"U.S. Appl. No. 11/316,120, Response filed May 14, 2008 to Non Final Office Action mailed Apr. 11, 2008", 12 pgs.
"U.S. Appl. No. 11/316,120, Response filed Aug. 27, 2010 to Non Final Office Action mailed May 27, 2010", 13 pgs.
"U.S. Appl. No. 11/394,601, Decision on Pre-Appeal Brief Request mailed Oct. 6, 2010", 2 pgs.
"U.S. Appl. No. 11/394,601, Notice of Allowance mailed Dec. 28, 2010", 8 pgs.
"U.S. Appl. No. 11/394,601, Pre-Appeal Brief Request filed Jul. 21, 2010", 5 pgs.
"U.S. Appl. No. 11/490,576, Final Office Action mailed Jan. 19, 2011", 12 pgs.
"U.S. Appl. No. 11/490,576, Pre-Appeal Brief Request filed May 12, 2011", 5 pgs.
"U.S. Appl. No. 11/490,576, Response filed Oct. 4, 2010 to Non Final Office Action mailed Jul. 12, 2010", 15 pgs.
"U.S. Appl. No. 11/490,916, Examiner Interview Summary mailed Apr. 12, 2010", 3 pgs.
"U.S. Appl. No. 11/490,916, Examiner Interview Summary mailed Aug. 19, 2009", 2 pgs.
"U.S. Appl. No. 11/490,916, Response filed Jan. 12, 2009 to Restriction Requirement Dec. 11, 2008", 7 pgs.
"U.S. Appl. No. 11/490,916, Supplemental Notice of Allowability Mailed Oct. 14, 2010", 2 pgs.
"U.S. Appl. No. 11/511,152, Notice of Allowance mailed Jul. 28, 2010", 6 pgs.
"U.S. Appl. No. 11/511,152, Preliminary Amendment filed Oct. 17, 2006", 3 pgs.
"U.S. Appl. No. 11/549,352, Examiner Interview Summary mailed Jun. 25, 2008", 2 pgs.
"U.S. Appl. No. 11/549,352, Examiner's Answer mailed Nov. 27, 2009 to Appeal Brief filed Sep. 9, 2009", 12 pgs.
"U.S. Appl. No. 11/549,352, Reply Brief filed Jan. 27, 2010", 8 pgs.
"U.S. Appl. No. 11/683,577, Examiner Interview Summary mailed Jul. 7, 2009", 4 pgs.
"U.S. Appl. No. 11/745,105, Non Final Office Action mailed May 11, 2011", 13 pgs.
"U.S. Appl. No. 11/745,105, Response filed Jul. 29, 2010 to Final Office Action mailed Mar. 30, 2010", 12 pgs.
"U.S. Appl. No. 12/361,884, Preliminary Amendment filed Jun. 30, 2011", 12 pgs.
"U.S. Appl. No. 12/910,106, Non Final Office Action mailed Apr. 4, 2011", 9 pgs.
"U.S. Appl. No. 12/910,106, Response filed Aug. 2, 2011 to Non-Final Office Action mailed Apr. 4, 2011", 14 pgs.
"European Application Serial No. 05815206.7, Response filed Apr. 19, 2010 to Communication Dec. 18, 2009", 27 pgs.
"European Application Serial No. 05815215.8, Response filed Mar. 19, 2010 to Communication mailed Dec. 18, 2009", 12 pgs.
"European Application Serial No. 05817448.3, Response filed Mar. 19, 2010 to Communication mailed Dec. 18, 2009", 9 pgs.
"European Application Serial No. 07759589.0, Summons to Attend Oral Proceedings mailed May 17, 2011", 3 pgs.
"Japanese Application Serial No. 2007-538087, Office Action mailed Apr. 11, 2011", (w/ English Translation), 5 pgs.
"Japanese Application Serial No. 2007-538087, Response filed Jun. 27, 2011 to Office Action dated Apr. 11, 2011", (w/ English Translation of Amended Claims), 12 pgs.
"Japanese Application Serial No. 2007-538088, Office Action mailed Jun. 13, 2011", (w/ English Translation), 5 pgs.
"Japanese Application Serial No. 2007-538089, Office Action mailed Mar. 3, 2011", (w/ English Translation), 6 pgs.
"Japanese Application Serial No. 2007-538089, Response filed May 25, 2011 to Office Action mailed Mar. 3, 2011", (w/ English Translation of Amended Claims), 8 pgs.

Tri-axial Coil Wound on Spiral Core

Transmit Circuit Block Diagram

LEADLESS CARDIAC STIMULATION SYSTEMS

CROSS-REFERENCE TO RELATED APPLICATION

This application is a divisional of U.S. application Ser. No. 10/971,550, filed Oct. 20, 2004 now U.S. Pat. No. 7,532,933, entitled LEADLESS CARDIAC STIMULATION SYSTEMS, which is hereby incorporated by reference.

TECHNICAL FIELD

This document relates to systems that electrically stimulate cardiac tissue and that do so without using leads that extend into the heart.

BACKGROUND

Pacemakers provide electrical stimulus to heart tissue to cause the heart to contract and hence pump blood. Conventionally, pacemakers include a pulse generator that is implanted, typically in a patient's pectoral region just under the skin. One or more leads extend from the pulse generator and into chambers of the heart, most commonly in the right ventricle and the right atrium, although sometimes also into a vein over the left chambers of the heart. An electrode is at a far end of a lead and provides the electrical contact to the heart tissue for delivery of the electrical pulses generated by the pulse generator and delivered to the electrode through the lead.

The conventional use of leads that extend from the pulse generator and into the heart chambers has various drawbacks. For example, leads have at their far ends a mechanism, such as tines or a "j-hook," that causes the lead to be secured to a tissue region where a physician positions the lead. Over time, the heart tissue becomes intertwined with the lead to keep the lead in place. Although this is advantageous in that it ensures the tissue region selected by the physician continues to be the region that is paced even after the patient has left the hospital, it is also disadvantageous in the event of a lead failure or in the event it is later found that it would be more desirable to pace a different location than the tissue region initially selected. Failed leads cannot always be left in the patient's body, due to any potential adverse reaction the leads may have on heart function, including infection, thrombosis, valve dysfunction, etc. Therefore, difficult lead removal procedures sometimes must be employed.

The conventional use of leads also limits the number of sites of heart tissue at which electrical energy may be delivered. The reason the use of leads is limiting is that leads most commonly are positioned within cardiac veins. As shown in FIG. 17, up to three leads 2, 3 and 4 are implanted in conventional pacing systems that perform multiple-site pacing of the heart 1, with the leads exiting the right atrium 5 via the superior vena cava 6. Multiple leads may block a clinically significant fraction of the cross section of the vena cava and branching veins leading to the pacemaker implant.

No commercial pacing lead has been indicated for use in the chambers of the left side of the heart. This is because the high pumping pressure on the left side of the heart may eject thrombus or clot that forms on a lead or electrode into distal arteries feeding critical tissues and causing stroke or other embolic injury. Thus, conventional systems, as shown in FIG. 17, designed to pace the left side of the heart thread a pacing lead 2 through the coronary sinus ostium 7, located in the right atrium 5, and through the coronary venous system 8 to a location 9 in a vein over the site to be paced on the left side. While a single lead may occlude a vein over the left heart locally, this is overcome by the fact that other veins may compensate for the occlusion and deliver more blood to the heart. Nevertheless, multiple leads positioned in veins would cause significant occlusion, particularly in veins such as the coronary sinus that would require multiple side-by-side leads.

There are several heart conditions that may benefit from pacing at multiple sites of heart tissue. One such condition is congestive heart failure (CHF). It has been found that CHF patients have benefited from bi-ventricular pacing, that is, pacing of both the left ventricle and the right ventricle in a timed relationship. Such therapy has been referred to as "resynchronization therapy." It is believed that many more patients could benefit if multiple sites in the left and right ventricles could be synchronously paced. In addition, pacing at multiple sites may be beneficial where heart tissue through which electrical energy must propagate is scarred or dysfunctional, which condition halts or alters the propagation of an electrical signal through that heart tissue. In these cases multiple-site pacing may be useful to restart the propagation of the electrical signal immediately downstream of the dead or sick tissue area. Synchronized pacing at multiple sites on the heart may inhibit the onset of fibrillation resulting from slow or aberrant conduction, thus reducing the need for implanted or external cardiac defibrillators. Arrhythmias may result from slow conduction or enlargement of the heart chamber. In these diseases, a depolarization wave that has taken a long and/or slow path around a heart chamber may return to its starting point after that tissue has had time to re-polarize. In this way, a never ending "race-track" or "circus" wave may exist in one or more chambers that is not synchronized with normal sinus rhythm. Atrial fibrillation, a common and life threatening condition, may often be associated with such conduction abnormalities. Pacing at a sufficient number of sites in one or more heart chambers, for example in the atria, may force all tissue to depolarize in a synchronous manner to prevent the race-track and circus rhythms that lead to fibrillation.

Systems using wireless electrodes that are attached to the epicardial surface of the heart to stimulate heart tissue have been suggested as a way of overcoming the limitations that leads pose. In the suggested system, wireless electrodes receive energy for generating a pacing electrical pulse via inductive coupling of a coil in the electrode to a radio frequency (RF) antenna attached to a central pacing controller, which may also be implanted. The wireless electrodes are screwed into the outside surface of the heart wall.

SUMMARY

The invention is directed to various configurations of systems that employ leadless electrodes to provide pacing therapy and that are commercially practicable. One of the findings of the inventors is that a significant issue to be considered in achieving a commercially practicable system is the overall energy efficiency of the implanted system. For example, the energy transfer efficiency of two inductively coupled coils decreases dramatically as the distance between the coils increases. Thus, for example, a transmitter coil implanted in the usual upper pectoral region may only be able to couple negligible energy to a small seed electrode coil located within the heart.

In one aspect of the invention, a system provides multiple sites for pacing of myocardium of a heart. The system includes wireless pacing electrodes that are implantable at sites proximate the myocardium using a percutaneous, transluminal, catheter delivery system. Each of the electrodes contains a source of electrical energy for pacing the myocardium and is adapted to receive electromagnetic energy from a source outside the myocardium. The system also includes a source adapted for placement outside the myocardium and that uses locally measured electrocardiograms to synchronize pacing of the heart by sending electromagnetic commands to the electrodes to pace the myocardium surrounding the electrodes.

In various embodiment, the system includes one or more of the following features. Each of the electrodes may contain a coil that is adapted to be inductively coupled to the source of electromagnetic energy. The source may be further adapted to charge, by inductive coupling electromagnetic energy at a first frequency common to all wireless electrodes, capacitors within the electrodes to provide the source of electrical energy for use in pacing the myocardium. A source of local energy proximate the electrodes may be used for pacing the myocardium, and the inductively coupled electromagnetic energy may include a command to release the local energy to pace the surrounding myocardium. In such a case, the source of electrical energy for use in pacing the myocardium is a battery may be contained within the wireless electrode. Also, the command to pace the myocardium may be an electromagnetic signal inductively coupled to each coil in each wireless electrode from the source of electromagnetic energy at a frequency that is unique for each implanted wireless electrode.

The source of electromagnetic energy may include an electronic control circuit, a transmit circuit, a battery, and an antenna. The source of electromagnetic may be implantable subcutaneously within the patient being paced. The source may be implantable within a chamber of the heart. The antenna may be implantable within a chamber of the heart, and the electronic control circuit, the transmit circuit and the battery may be implantable outside of the heart. The locally measured electrocardiogram may be a voltage sensed by the electrodes proximate the source. The battery may be rechargeable. Energy to recharge the battery may be electromagnetic energy inductively coupled to the antenna from a source outside the body.

The source of electromagnetic energy may be wearable outside of the body of the patient being paced. For example, the source may be either wearable in the patient's clothing or contained in a disposable patch attached to the patient's torso. The local electrocardiogram may be a voltage measured by one or more wireless electrodes and inductively communicated to the source. The electrocardiogram may be measured at the electrodes of a conventional pacemaker and communicated to the source outside the myocardium through an inductive link. The electromagnetic energy commanding the electrodes to pace may be received by one wireless electrode, and all other wireless electrodes may pace local myocardium in response to changes in the electrocardiogram measured by each electrode at the site of each electrode. In further embodiments of the systems, neighboring wireless electrodes may be inductively coupled to each other, and inductively received signals from neighboring wireless electrodes may determine in part the time that said electrode paces local myocardium.

In another aspect of the invention, a catheter delivery system is provided for implanting wireless electrodes into the myocardium. The catheter delivery system includes an elongate tube having a proximal end and a distal end and having a lumen passing through the elongate tube. The delivery system also includes an elongate rod having a proximal end and a distal end with a wireless electrode attached to its distal end. The rod includes a detachment mechanism to detach the wireless electrode from the rod following delivery of the wireless electrode to the myocardium. The rod with an attached wireless electrode is passable through the tube for delivery to the myocardium.

In various embodiment, the catheter delivery system may have one or more of the following features. The elongate tube may contains a steering mechanism, such as push or pull wires, to aid in placement of the distal end of the tube against a selected site on the wall of the heart. The elongate tube may contain an electrode at its distal end for sensing the local electrocardiogram at the selected site on the wall of the heart.

In another aspect of the invention, an implantable wireless electrode is provided for pacing a site proximate the myocardium. The electrode includes a source of electrical energy for use in pacing the myocardium, a receiver to receive electromagnetic energy from a source external of the myocardium, and an attachment mechanism to attach the electrode to the myocardium to prevent migration.

In various embodiment, the implantable wireless electrode may have one or more of the following features. The source of electrical energy may be derived from a physiological source of energy proximate the wireless electrode when implanted and that is transduced to electrical energy within the wireless electrode. The source of electrical energy may be external to the myocardium and inductively coupled to a coil that is proximate to and connected to the wireless electrode. The receiver may be a coil that resides within the wireless electrode, or alternatively may reside proximate the myocardium but outside of the wireless electrode. The receiver may be a coil that is proximate to and connected to the wireless electrode.

In addition, the received electromagnetic energy may be a signal commanding the wireless electrode to deliver the source of electrical energy to pace the surrounding myocardium. The signal may include electromagnetic energy having a frequency that is unique for each wireless electrode. The source of electrical energy may be inductively coupled from a source external to the myocardium and stored on a capacitor contained within the wireless electrode. The capacitor may be isolated from said coil when the capacitor voltage reaches a predetermined reference value. The predetermined voltage may be less than 5 volts. A received signal may reset the predetermined voltage, and may command the capacitor to discharge through surrounding myocardium. The attachment mechanism may consist of tines, screws, barbs, hooks, and other fasteners that secure the body of the wireless electrode to the myocardium.

In another aspect of the invention, a method is provided for delivering a wireless electrode to a location proximate the myocardium. The method includes delivering an elongate member having a proximal end and a distal end and a lumen therethrough to a site proximate the myocardium, delivering a wireless electrode attached to a rod through the lumen of the elongate member and into the myocardium proximate the distal end of the elongate member, enabling a detachment mechanism to detach the rod from the wireless electrode, and removing the rod and the catheter from the body of the patient.

In various embodiments, the method may include one or more of the following features. A local electrocardiogram may be measured at the distal end of the elongate member to determine the suitability of the site proximate the myocardium for pacing. A tube may be threaded over the rod but inside the lumen of the elongate member, and the tube may abut the proximal end of the wireless electrode to push the electrode through the lumen. A short burst of current may be applied to the rod to heat and detach the rod at a spot on the rod having relatively high electrical resistance.

In another aspect of the invention, a method is provided for synchronizing the contraction of a beating heart within a patient. The method includes delivering a plurality of wireless electrodes to locations proximate the myocardium through a catheter delivery system, monitoring a physiologic measure of heart function and selecting the timing and sequence of pacing of the plurality of wireless electrodes to optimize the measure of heart function, and programming a pacing sequence into a controller.

In various embodiments, the method may include one or more of the following features. The measure of heart function may be cardiac output, ejection fraction, rate of pressure of diastole, or a combination of these measures. The controller may be implanted subcutaneously into the patient. Alternatively, the controller may be worn in clothing or within a patch on the outside of the patient's body. Further yet, the controller may be implanted within a chamber of said heart.

In another aspect of the invention, a system is provided for use with multiple body implanted wireless electrode assemblies that each have a pair of electrodes that are in contact with tissue of a body vessel. Each of the electrode assemblies may be charged by inductive coupling and subsequently discharged to deliver electrical energy across the pair of electrodes and thus across the contacted body tissue. The system includes an implantable controller that senses electrical activity occurring within the body vessel and that determines from such sensing a timing of when electrical energy is to be delivered by each of the wireless electrode assemblies. The system also includes a wireless transmitter and associated power source and antenna, wherein the transmitter is controllable by the implantable controller to charge, by inductive coupling, the storage capacitors of the implanted wireless electrode assemblies, and to provide wireless control signals that trigger the discharge of the storage capacitor in a specified one of the wireless electrode assemblies.

In various embodiments, the system may include one or more of the following features. The wireless transmitter and associated antenna may be adapted to be implanted within a body. The wireless transmitter and the controller may be provided within a single housing, which may, for example, be shaped for implantation between ribs. A battery may be provided within the single housing for providing power for the wireless transmitter, and the controller may be rechargeable. The single housing may alternatively be shaped for placement on a ventricular septum. Again in this case, a battery may be provided within the single housing for providing power for the wireless transmitter, and the controller may be rechargeable.

In addition, the wireless transmitter and associated antenna may be adapted to be worn external of a body. The controller may be adapted to be implanted within a body. The implantable controller may communicate wirelessly with the external wireless transmitter and associated antenna. The implantable controller may be programmable by external programmer. The wireless control signals provided by the wireless transmitter may have multiple frequencies, with each of the multiple frequencies specifying one of the multiple wireless electrode assemblies. The body vessel may be a heart. The controller may have electrodes to sense electrical activity occurring within the body vessel.

In yet another aspect of the invention, a body implantable electrode assembly is provided that includes a charge storage device operatively coupled to deliver stored charge discharged from the charge storage device across a pair of electrodes that are positionable to be in contact with body tissue. The electrode assembly also includes a receiver coil that inductively couples an externally provided charging signal to charge the charge storage device and that receives externally provided wireless control signals. The electrode assembly also includes control circuitry that triggers the discharge of stored charge from the charge storage device upon receipt of a wireless control signal that indicates that the storage capacitor is to be discharged and that includes information that identifies the body implantable electrode assembly from among other such body implantable electrode assemblies.

In various implementations, the body implantable electrode assembly may have one or more of the following features. The wireless control signal may identify the electrode. The electrode assembly may be tuned to respond to a particular frequency of wireless control signal. The electrode assembly may have a filter that filters all but a selected frequency. The electrode assembly may also include a mechanism that secures the assembly to body tissue. The electrode assembly may not include an internally generated power source.

In another aspect of the invention, a method is provided for controlling the delivery of electrical signals from a plurality of wireless electrode assemblies that each have a pair of electrodes that are in contact with tissue of a body vessel. Each of electrode assemblies may be charged by inductive coupling and subsequently discharged to deliver electrical energy across the pair of electrodes and contacting body tissue. The method includes wirelessly transmitting a charging signal that is received by each of the plurality of the wireless electrode assemblies to charge each of the storage capacitors of the plurality of wireless electrode assemblies at the same time, and wirelessly transmitting control signals that are received by the wireless electrode assemblies to trigger the discharge of the storage capacitor in a selected one of the wireless electrode assemblies.

In various implementations, the method may include one or more of the following features. The wirelessly transmitted control signals may be transmitted at different frequencies, wherein one of the different frequencies identifies the selected one of the wireless electrode assemblies.

In another aspect of the invention, a catheter is provided for manipulating a body implantable wireless electrode assembly. The catheter includes an elongate tube with a lumen extending longitudinally therethrough to an opening at a distal end of the tube. The lumen is sized so that a wireless electrode assembly may be moved through the tube lumen and out the distal opening of the tube. The catheter also includes an elongate member that slidably fits within the tube lumen and that is controllable to move a seed electrode distally within the tube lumen and out the distal opening of the tube lumen for positioning within the lumen body. The elongate member has a lumen extending longitudinally therethrough and constructed so that a lead that is detachably connected to the seed-type electrode of the seed-type electrode assembly extends proximally through the elongate member lumen and out a proximal port of the catheter so that electrical signals sensed by the electrode are provided external of the body.

In another aspect of the invention, a body implantable wireless electrode assembly is provided that includes a pair of electrodes that contact tissue of a vessel, securing mechanism that secures the assembly to body tissue in a selected position of the vessel, a lead that is detachably connected to one of the pair of electrodes such that during an implantation procedure wherein the lead extends outside the body and allows electrical activity sensed by the connected electrode to be externally monitored, and a detachment mechanism that when actuated detaches the lead from the wireless electrode assembly.

In various implementations, the implantable wireless electrode assembly may include one or more of the following features. The electrode assembly may further include a lead connected to one of the pair of electrodes that first contacts tissue during an implantation procedure. One of the pair of electrodes may be provided on one end of the electrode assembly, and the electrode assembly may have an electrical conductor extending within the assembly to an opposite end of the assembly. The lead may be physically connected to the conductor.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This document describes various configurations of systems that employ leadless electrodes to provide pacing therapy and that are commercially practicable. One of the findings of the inventors is that a significant issue to be considered in achieving a commercially practicable system is the overall energy efficiency of the implanted system. For example, the energy transfer efficiency of two inductively coupled coils decreases dramatically as the distance between the coils increases. Thus, for example, a transmitter coil implanted in the usual upper pectoral region may only be able to couple negligible energy to a small seed electrode coil located within the heart.

Figure 1:
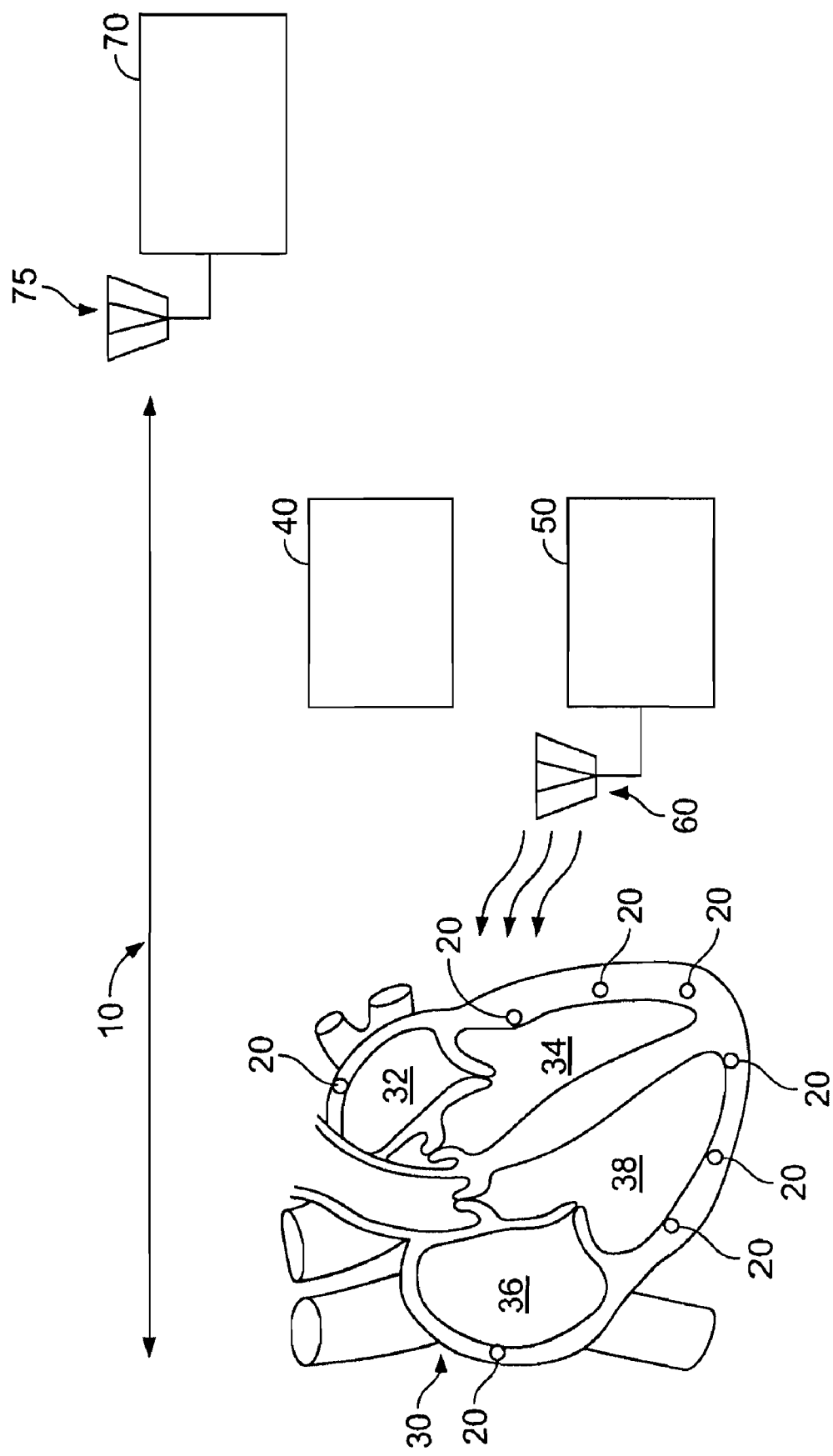
FIG. 1 is a conceptual diagram of a leadless cardiac stimulation system (with leadless, or wireless, electrode assemblies shown implanted in a heart) and of an external programmer.

FIG. 1 shows a general depiction of such a system 10 and an external programming device 70. The system 10 includes a number of wireless electrode assemblies 20, herein referred to simply as "seeds." The seeds 20 are implanted within chambers of the heart 30. In this example, there are eight seeds 20, there being one implanted in the left atrium 32, three implanted in the left ventricle 34, one implanted in the right atrium 36, and three implanted in the right ventricle 38. In one embodiment, each of the seeds 20 has an internal coil that is inductively coupled with an external power source coil to charge an electrical charge storage device contained within the seed 20, and also has a triggering mechanism to deliver stored electrical charge to adjacent heart tissue.

The system 10 also includes a pacing controller 40 and a transmitter 50 that drives an antenna 60 for communication with the seeds 20. Generally, the pacing controller 40 includes circuitry to sense and analyze the heart's electrical activity, and to determine if and when a pacing electrical pulse needs to be delivered and by which of the seeds 20. The sensing capability may be made possible by having sense electrodes included within the physical assembly of the pacing controller 40. Alternatively, a conventional single or dual lead pacemaker (not shown in FIG. 1; although see FIG. 2B) may sense the local cardiac electrocardiogram (ECG) and transmit this information to antenna 60 for use by controller 40 in determination of the timing of seed firing. In either case, the seed 20 need not be provided with sensing capability, and also the seeds 20 need not be equipped with the capability of communicating to the pacing controller 40 (for example, to communicate information about sensed electrical events). In alternative embodiments, the seeds may communicate sensed information to each other and/or to the controller 40.

The transmitter 50—which is in communication with, and is controlled by, the pacing controller 40—drives an RF signal onto the antenna 60. In one embodiment, the transmitter 50 provides both 1) a charging signal to charge the electrical charge storage devices contained within the seeds 20 by inductive coupling, and 2) an information signal, such as a pacing trigger signal, that is communicated to a selected one or more of the seeds 20, commanding that seed to deliver its stored charge to the adjacent tissue.

An important parameter of the seed 20 that is a driver of the system 10 design is the maximum energy required to pace the ventricle. This energy requirement includes a typical value needed to pace ventricular myocardium, but also includes a margin to account for degradation of contact between the electrodes and tissue over time. It must be assumed that each seed may require the maximum pacing threshold energy. This threshold energy must be supplied to the seeds between heartbeats by an external radio frequency generator (which may also be implanted), or other suitable energy source that may be implanted within the body. Typical values are:

Threshold pacing voltage=2.5 Volts
Typical lead impedance=600 Ohms
Typical pulse duration=0.4 mSec
Derived threshold energy=4 micro-Joules Because RF fields at frequencies higher than about 100 kHz are attenuated by the body's electrical conductivity, and because electric fields of any frequency are attenuated within the body, energy transmission through the body may be accomplished via a magnetic field at about 20-100 kHz (or by a magnetic field pulse that contains major frequency components in this range), and preferably by transmission of magnetic fields in the range of 20-30 kHz when transmission is through relatively conductive blood and heart muscle.

As will be seen later in some of the specifically described configurations of the system 10, the pacing controller 40 and the transmitter 50 may be housed in a single enclosure that is body implantable within a patient. In such a configuration the single enclosure device may have a single energy source (battery) that may be either rechargeable or non-rechargeable. In another configuration, the pacing controller 40 and the transmitter 50 may be physically separate components. As an example of such a configuration, the pacing controller 50 may be implantable, for example in the conventional pacemaker configuration, whereas the transmitter 50 (along with the antenna 60) may be adapted to be worn externally, such as in a harness that is worn by the patient. In the latter example, the pacing controller 40 would have its own energy source (battery), and that energy would not be rechargeable given the relatively small energy requirements of the pacing controller 40 as compared to the energy requirements of the transmitter 50 to be able to electrically charge the seeds 20. In this case, the pacing controller 40 would sense the local cardiac ECG signal through a conventional pacing lead, and transmit the sensed information to the external controller. Again, transmission of information, as opposed to pacing energy, has a relatively low power requirement, so a conventional pacemaker enclosure and battery would suffice.

The external programmer 70 is used to communicate with the pacing controller 40, including after the pacing controller 40 has been implanted. The external programmer 70 may be used to program such parameters as the timing of stimulation pulses in relation to certain sensed electrical activity of the heart, the energy level of stimulation pulses, the duration of stimulation pulse (that is, pulse width), etc. The programmer 70 includes an antenna 75 to communicate with the pacing controller 40, using, for example, RF signals. The implantable pacing controller 40 is accordingly equipped to communicate with the external programmer 70, using, for example, RF signals. The antenna 60 may be used to provide such communications, or alternatively, the pacing controller 40 may have an additional antenna (not shown in FIG. 1) for external communications with the programmer 70, and in an embodiment where the transmitter 50 and antenna 60 are housed separately from the controller 40, for communications with the transmitter 50.

Figure 2A:
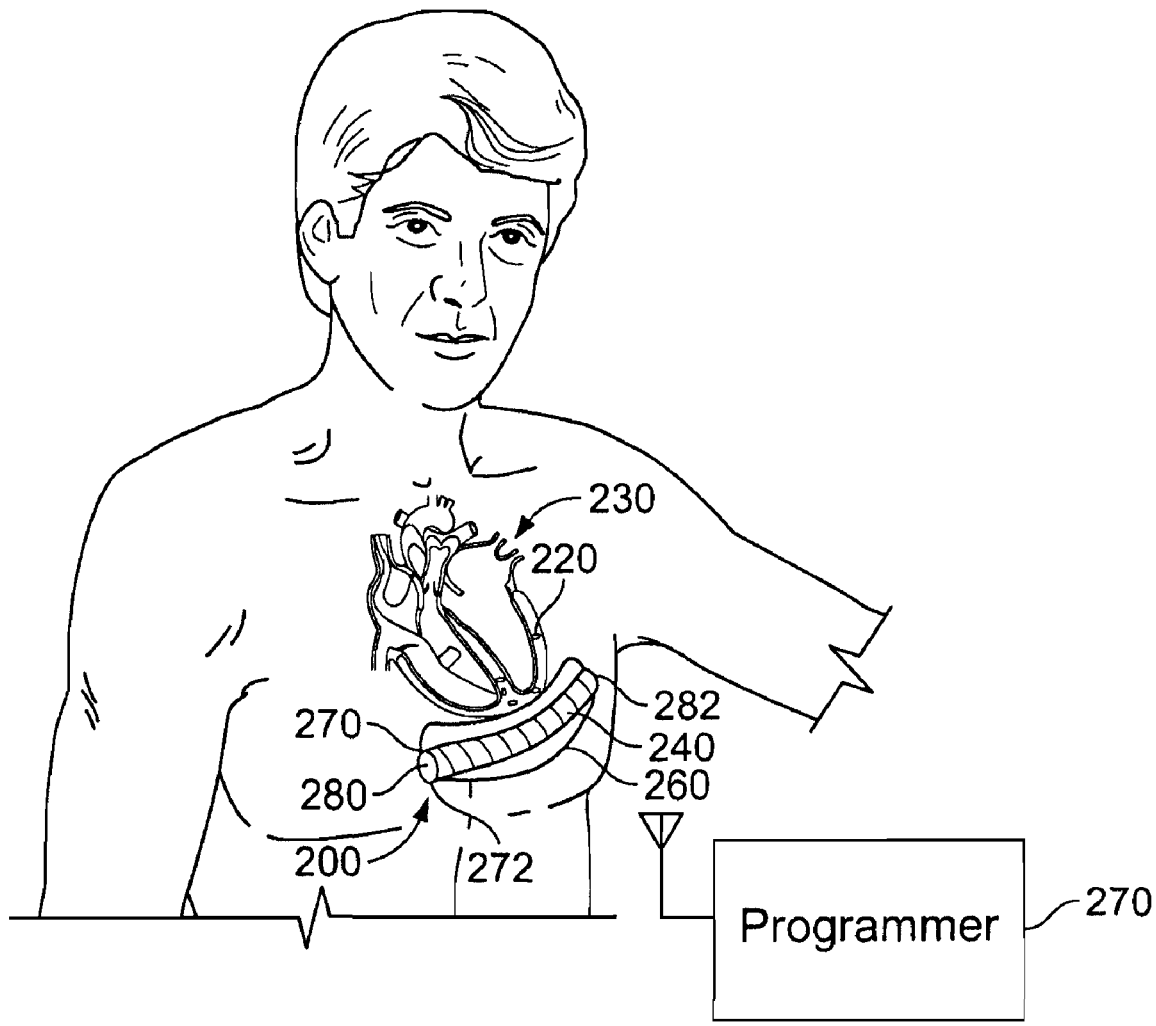
FIGS. 2A and 2B are diagrams example systems of the type shown in FIG. 1, and shown implanted in a body.

FIG. 2A shows an example system 200 of the type shown in FIG. 1. The system 200 is shown as having been implanted in a patient, and in addition, a programmer 270 is also shown that is external to the patient. As shown, the system 200 is of a type that is entirely implantable. The system 200 includes several seed electrode assemblies 220, there being four such assemblies shown as having been implanted within the heart 230 in FIG. 2A. The system 200 also includes an implantable combined pacing controller and transmitter device 240 that has an antenna 260 for communicating, for example, to the seeds 220. The controller/transmitter device 240 is shaped generally elongate and slightly curved so that it may be anchored between two ribs of the patient, or possibly around two or more ribs. In one example, the controller/transmitter device 240 is 2 to 20 cm long and 1 to 10 centimeters (cm) diameter, preferably 5 to 10 cm long and 3 to 6 cm diameter. Such a shape of the controller/transmitter device 240, which allows the device 240 to be anchored on the ribs, allows an enclosure that is larger and heavier than conventional pacemakers, and allows a larger battery having more stored energy.

The antenna 260 in the FIG. 2A example is a loop antenna consisting of a long wire whose two ends 270 and 272 extend out of the housing of the controller/transmitter device 240 at one end 280 of the controller/transmitter device 240. The opposite ends 270 and 272 of the loop antenna 260 are electrically connected across an electronic circuit contained within the controller/transmitter device 240, which circuit delivers pulses of RF current to the antenna, generating a magnetic field in the space around the antenna to charge the seeds, as well as RF control magnetic field signals to command the seeds to discharge. The loop antenna 260 may be made of a flexible conductive material so that it may be manipulated by a physician during implantation into a configuration that achieves the best possible inductive coupling between the antenna 260 and the coils within the implanted seeds 220. In one example, the loop antenna 260 may be 2 to 22 cm long, and 1 to 11 cm wide, preferably 5 to 11 cm long, and 3 to 7 cm wide. Placement of the antenna over the ribs allows a relatively large antenna to be constructed that has improved efficiency in coupling RF energy to the pacing seeds.

In FIG. 2A, the loop antenna 260 has been configured to extend generally around the periphery of the housing of the controller/transmitter device 240. In particular, the loop antenna 260 extends from its first end 270 (located at the first end 280 of the controller/transmitter device 240) outwardly and then generally parallel to the elongately shaped controller/transmitter device 240 to the second end 282 of the controller/transmitter device 240. From there, the loop antenna 260 extends outwardly and again generally parallel to the controller/transmitter device 240, albeit on an opposite side of the transmitter/controller device 240, and back to the first end 280 of the controller/transmitter device 240. As such, the loop antenna 260 may, like the controller/transmitter device 240, be anchored to the ribs of the patient.

In this configuration, the distance between the center of the loop antenna 260 and the seed electrode assemblies 220 will typically be, on average, about three inches (3"). As will be shown later, such a distance puts significant power demands on the controller/transmitter device 240, and so an internal battery included within the controller/transmitter device 240 may need to be rechargeable. In some embodiments, however, the controller/transmitter device 240 may be non-rechargeable. The loop antenna 260 may have a shape that is more complex than that shown in FIG. 2, with a larger antenna area, or multiple antenna lobes to capture more tissue volume. The antenna may consist of two or more wire loops, for example, one on the front of the patient's rib cage, and a second on the back, to gain magnetic field access to a larger tissue region.

Figure 2B:
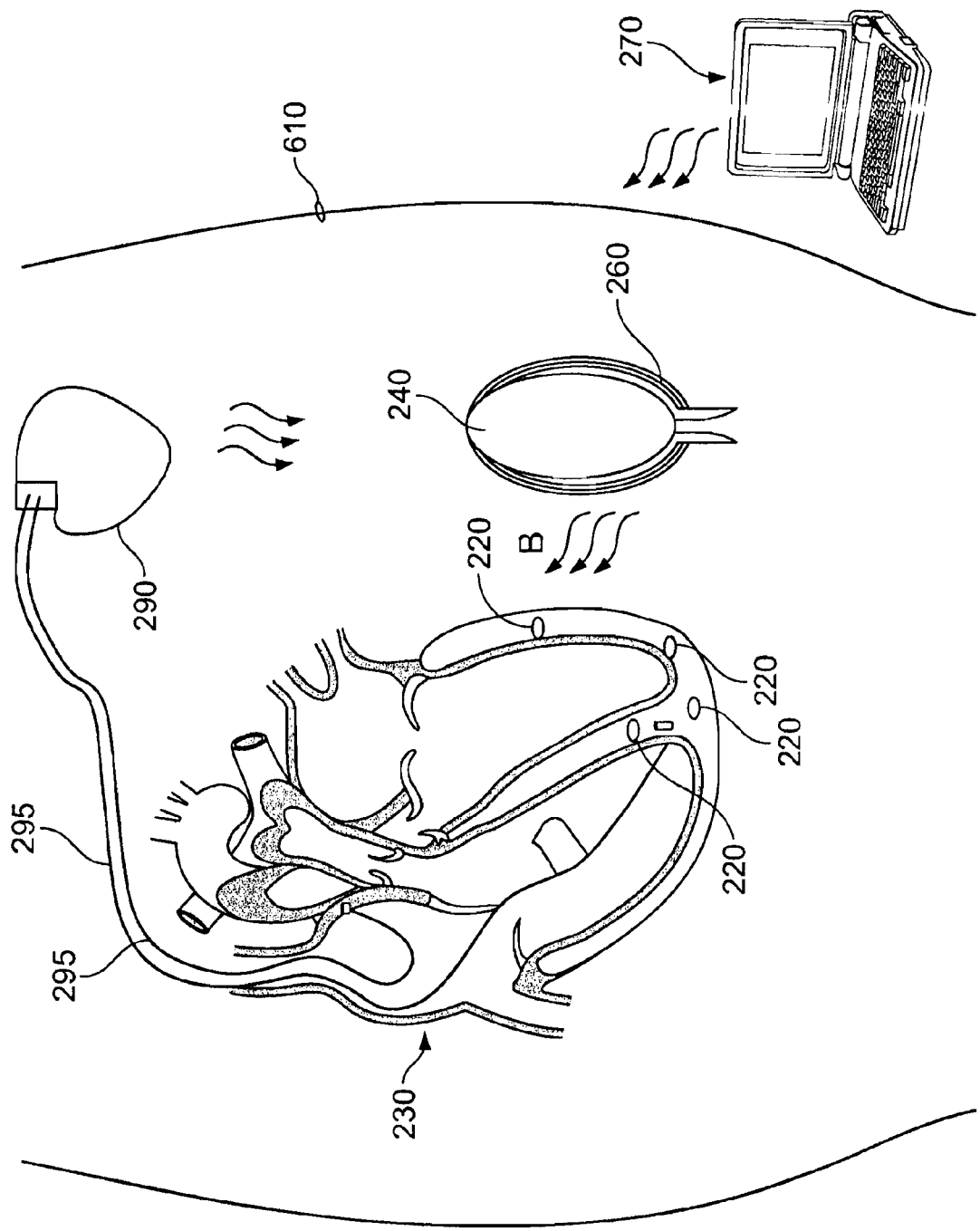

Referring to FIG. 2B, there is shown an embodiment as shown in FIG. 2A, but which also includes a conventional pacemaker, or pulse generator, 290 and associated wired leads 295 which extend from the pulse generator 290 and into chambers of the heart 600. As such, the pulse generator 290 may be used to sense the internal ECG, and may also communicate with the controller/transmitter 240 as discussed previously.

Figure 3:
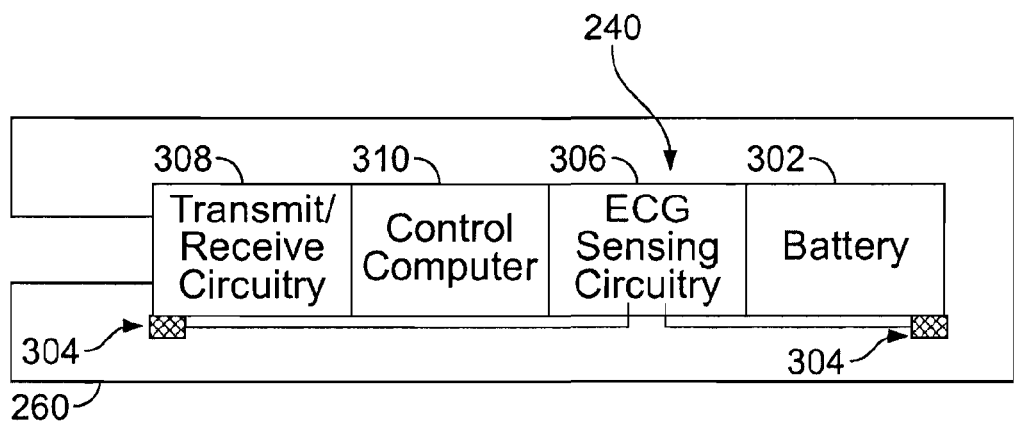
FIG. 3 is a block diagram of an example embodiment of a combined controller/transmitter device and associated antenna that may be used as part of the FIG. 2A or 2B system.

Referring to FIG. 3, an embodiment of the controller/transmitter 240 and associated loop antenna 260 is shown in block diagram form. Included within the pacing controller 240 is: a battery 302, which may be recharged by receiving RF energy from a source outside the body via antenna 260; ECG sensing electrodes 304 and associated sensing circuitry 306; circuitry 308 for transmitting firing commands to the implanted seeds, transmitting status information to the external programmer, receiving control instructions from the external programmer and receiving power to recharge the battery; and a computer 310 that is programmed to control the overall functioning of the pacing control implant. In alternative embodiments, antenna 260 may receive signals from the individual seeds 220 containing information regarding the local ECG at the site of each seed, and/or antenna 260 may receive signals from a more conventional implanted pacemaker regarding the ECG signal at the sites of one or more conventional leads implanted on the right side of the heart.

Figure 4:
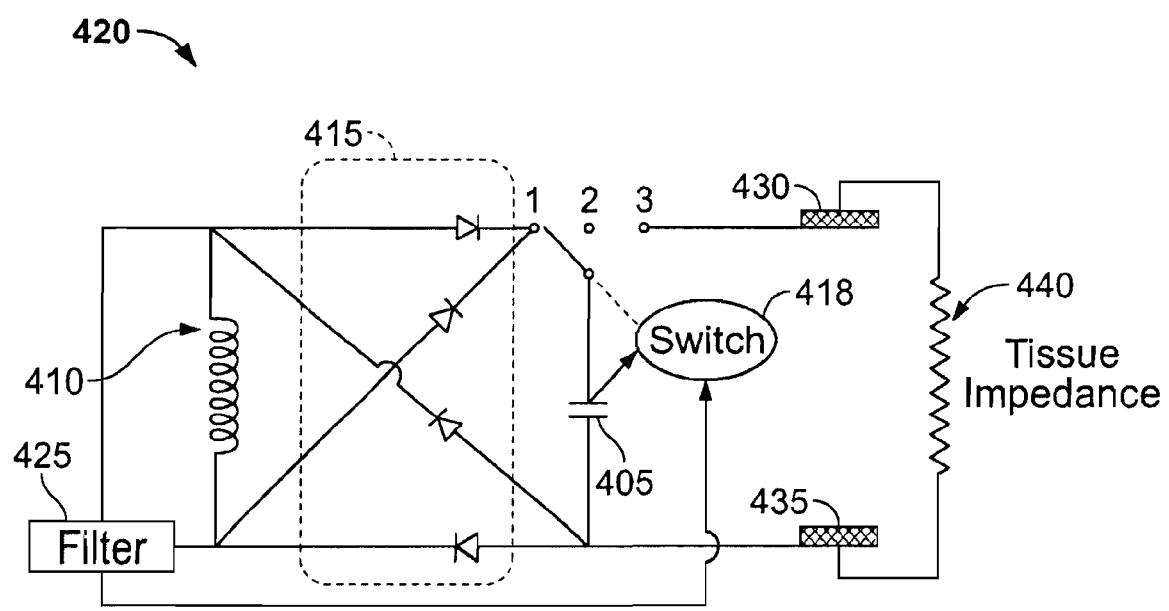
FIG. 4 is a schematic diagram of a portion of the circuitry included in a wireless electrode assembly as is shown in FIGS. 1 and 2A-B.

FIG. 4 is a schematic diagram of an example wireless electrode assembly, or seed, 420, which may serve as the seeds 20 or 220 as shown in either FIG. 1 or FIGS. 2A-B. The seed 420 includes, firstly, a receiver coil 410 that is capable of being inductively coupled to a magnetic field source generating a time-varying magnetic field at the location of coil 410, such as would be generated by the transmitter 50 and the antenna 60 shown in FIG. 1. The RF current in the external antenna may be a pulsed alternating current (AC) or a pulsed DC current, and thus the current induced through the receiver coil 410 would likewise be an AC or pulsed DC current. The current induced in coil 410 is proportional to the time rate of change of the magnetic field generated at the site of coil 410 by the external RF current source. A four-diode bridge rectifier 415 is connected across the receiver coil 410 to rectify the AC or pulsed DC current that is induced in the receiver coil 410. A three-position switch device 418 is connected so that when the switch device 418 is in a first position, the rectifier 415 produces a rectified output that is imposed across a capacitor 405. As such, when the switch device 418 is in the position 1 (as is the case in FIG. 4), the capacitor 405 stores the induced electrical energy.

The switch device 418, in this example, is a voltage-controlled device and is connected to sense a voltage across the capacitor 405 to determine when the capacitor 405 has been sufficiently charged to a specified pacing threshold voltage level. When the capacitor 405 is sensed to have reached the specified pacing threshold level, the voltage-controlled switch device 418 moves to a position 2, which disconnects the capacitor 405 from the coil 510. With the switch device 418 in the position 2, the capacitor 405 is electrically isolated and remains charged, and thus is ready to be discharged. The voltage controlled switch device 418 may consist of a solid state switch, such as a field effect transistor, with its gate connected to the output of a voltage comparator that compares the voltage on capacitor 405 to a reference voltage. The reference voltage may be set at the factory, or adjusted remotely after implant via signals sent from the physician programmer unit, received by coil 410 and processed by circuitry not shown in FIG. 4. Any electronic circuitry contained within the seed, including the voltage controlled switch, is constructed with components that consume very little power, for example CMOS. Power for such circuitry is either taken from a micro-battery contained within the seed, or supplied by draining a small amount of charge from capacitor 405.

A narrow band pass filter device 425 is also connected across the receiver coil 410, as well as being connected to the three-position switch device 418. The band pass filter device 425 passes only a single frequency of communication signal that is induced in the coil 410. The single frequency of the communication signal that is passed by the filter device 425 is unique for the particular seed 20 as compared to other implanted seeds. When the receiver coil 410 receives a short magnetic field burst at this particular frequency, the filter device 425 passes the voltage to the switch device 418, which in turn moves to a position 3.

With the switch device in the position 3, the capacitor 405 is connected in series through two bipolar electrodes 430 and 435, to the tissue to be stimulated. As such, at least some of the charge that is stored on the capacitor 405 is discharged through the tissue. When this happens, the tissue becomes electrically depolarized. In one example embodiment that will be shown in more detail later, the bipolar electrodes 430 and 435 across which stimulation pulses are provided are physically located at opposite ends of the seed 420. After a predetermined, or programmed, period of time, the switch returns to position 1 so the capacitor 405 may be charged back up to the selected threshold level.

It should be noted that, for sake of clarity, the schematic diagram of FIG. 4 shows only the seed electrical components for energy storage and switching. Not shown are electronics to condition the pacing pulse delivered to the tissues, which circuitry would be known to persons skilled in the art. Some aspects of the pulse, for example pulse width and amplitude, may be remotely programmable via encoded signals received through the filter device 425 of the seed 420. In this regard, filter 425 may be a simple band pass filter with a frequency unique to a particular seed, and the incoming signal may be modulated with programming information. Alternatively, filter 425 may consist of any type of demodulator or decoder that receives analog or digital information induced by the external source in coil 410. The received information may contain a code unique to each seed to command discharge of capacitor 405, along with more elaborate instructions controlling discharge parameters such as threshold voltage for firing, duration and shape of the discharge pulse, etc.

Using seeds of the type shown in FIG. 4, all of the implanted seeds may be charged simultaneously by a single burst of an RF charging field from a transmitter antenna 60. Because back reaction of the tiny seeds on the antenna 60 is small, transmitter 50 (FIG. 1) losses are primarily due to Ohmic heating of the transmit antenna 60 during the transmit burst, Ohmic heating of the receive coil 410, and Ohmic heating of conductive body tissues by eddy currents induced in these tissues by the applied RF magnetic field. By way of comparison, if eight seeds are implanted and each is addressed independently for charging, the transmitter 50 would be turned ON eight times as long, requiring almost eight times more transmit energy, the additional energy being primarily lost in heating of the transmit antenna 60 and conductive body tissues. With the seed 420 of FIG. 4, however, all implanted seeds are charged simultaneously with a burst of RF current in antenna 260, and antenna and body tissue heating occurs only during the time required for this single short burst. Each seed is addressed independently through its filter device 425 to trigger pacing. The transmitted trigger fields can be of much smaller amplitude, and therefore lose much less energy to Ohmic heating, than the transmitted charging pulse.

Figure 5:
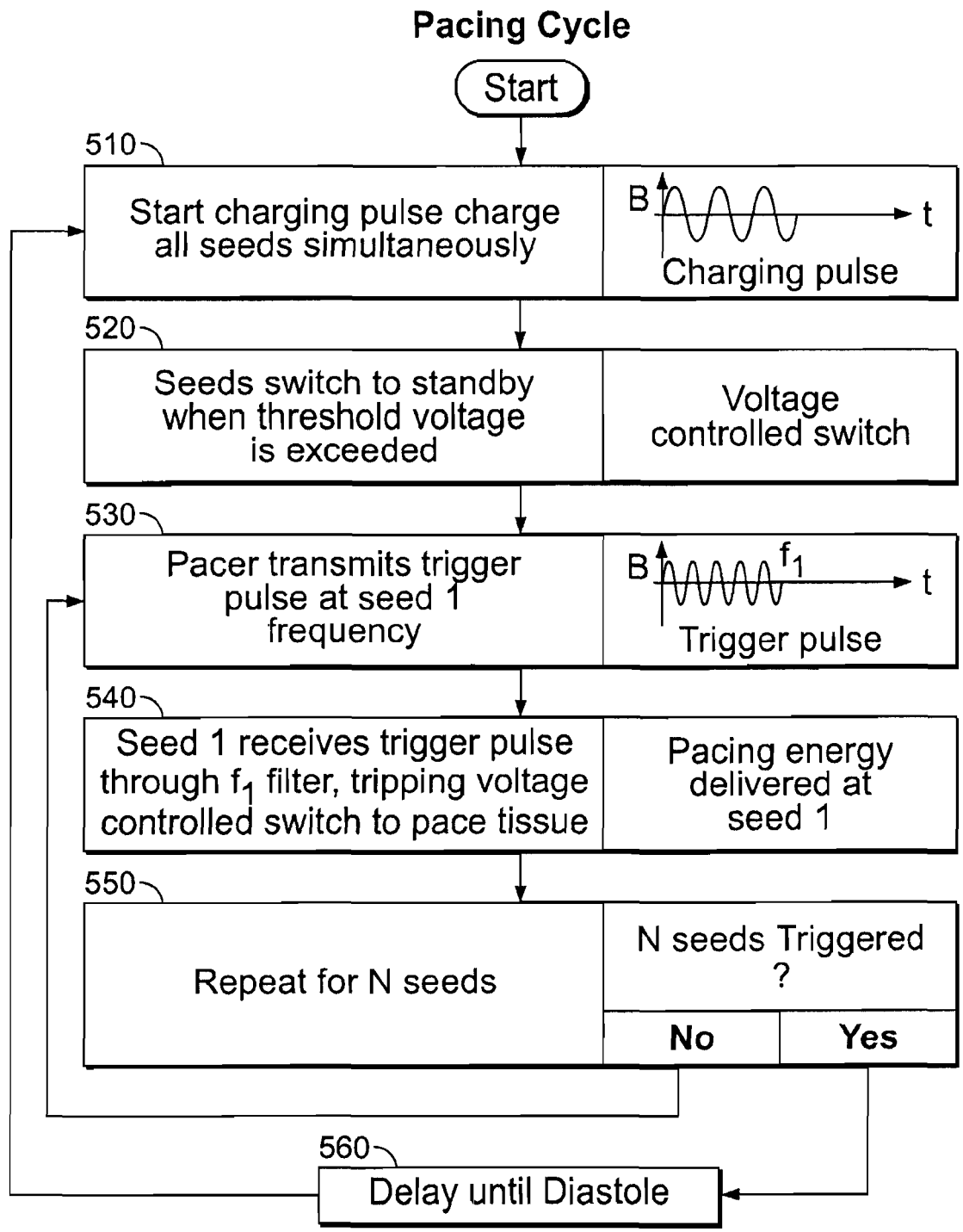
FIG. 5 is a flow chart of a method of providing stimulation pulses in a pacing cycle in a system such as shown in FIGS. 1 and 2A-B.

FIG. 5 is a flowchart of a pacing cycle that shows such a mode of operation of charging all implanted seeds 20 simultaneously, and triggering the discharge of each seed 20 independently. The method starts at step 510 with the start of a charging pulse that charges all of the seeds simultaneously. When a pacing threshold voltage is attained or exceeded, at step 520, the seeds switch to a standby mode (for example, switch 418 in seed 420 moves to position 2). Next, in step 530, at the appropriate time, a controller/transmitter device such as device 240 shown in FIG. 2, transmits a trigger pulse at a particular frequency (f1) that is passed through a band pass filter (such as filter device 425) in the seed to be fired (for example, seed 1). Then, at step 540, that seed, namely seed 1, receives the trigger pulse through the band pass filter, which in turn trips the switch to pace the tissue. This process may be repeated for each of the N number of seeds that have been implanted, as indicated at step 550, which returns to step 530 where there are additional seeds that have been charged and are to be fired. Next, at step 560 there is a delay until the next diastole, after which time the process begins anew at step 510. The exact time of firing of the first seed is programmed by the physician in relation to the ECG signal features measured by the sensing electrodes 304 in FIG. 3, or in relation to ECG information transmitted to the controller 240 by the pacing seeds themselves, or in relation to pacing information transmitted to the controller 240 by a conventional implanted pacemaker, or in relation to pacing information received from a conventional implanted pacemaker through an implanted hard wire connection to controller 240. Subsequent timing of the firing of each additional seed is programmed by the physician at the time of implant. Note that seeds may be programmed not to discharge. For example, an array of seeds may be implanted, but only a subset may be programmed to receive firing commands from the controller 240.

In the case of FIG. 2A and other similar embodiments, it is envisioned that the controller/transmitter device 240 and associated antenna 260 would first be implanted subcutaneously in a designed location (for example, between the ribs in the case of the FIG. 2A embodiment). The physician then may program the controller/transmitter 240 by delivering telemetric signals through the skin using the programmer 270 in a conventional manner, although this programming may also be done, at least in part, before implantation. One of the adjustable parameters is the timing of firing of each seed 220, determined by a time at which a short burst of current at the frequency for the particular seed 220 is delivered to the antenna 260. The controller/transmitter device 240 may have a pair of sensing electrodes on its surface to detect the subcutaneous electrocardiogram (ECG), or it may contain multiple electrodes to provide a more detailed map of electrical activity from the heart. This local ECG signal sensed by the controller/transmitter device 240 may be used to trigger the onset of seed pacing when the patient has a functioning sinus node. In any case, the signals sensed by the controller/transmitter device 240 are used to monitor ECG signals from the paced heart. In some cases, these ECG signals, or other physiologic sensor input signals, may be used to adjust or adapt the timing of firing of the pacing seeds 220.

Alternatively, the controller 240 may receive local ECG or pacing information through an RF link from a conventional pacemaker 290 implanted in the pectoral region of the patient, as shown in FIG. 2B. This may be desirable in patients who already have a conventional pacemaker, or when local ECG data from the conventional atrial or right ventricular apex pacing sites are desired to coordinate the timing of firing of the implanted seeds 220. Finally, the seeds 220 could themselves transmit information to controller 240 concerning the local bi-polar ECG measured at their sites. Alternatively, the seeds 220 could sense the local ECG and discharge based upon this local data, with no firing instructions from the controller 240 required, or the seeds 220 could transmit information from seed 220 to seed concerning local ECG and onset of their discharge. All of the above embodiments, or a subset, may be implemented in this invention.

In an example embodiment, the seeds 220 would be delivered to their respective sites in the cardiac veins, within the heart wall, or on the epicardial surface of the heart via a catheter, as will be described in more detail later. A distal portion, or tip of the catheter, may contain a single electrode or a pair of electrodes, each being connected to a signal recorder via leads extending to a proximal end of the catheter. As such, it is possible to obtain a uni-polar or bipolar ECG at the catheter distal tip. The physician would select the implantation site based upon features of the ECG signal sensed using the catheter. The seed then may be injected through a needle extended from the catheter tip, or it may be pushed into the tissue and then released from the catheter. Many mechanisms may be used for seed release, including the release or addition of fluid pressure to the catheter tip.

Once implanted, the seed 220 may be charged and then fired to observe the altered electrogram proximate the seed at the location of the catheter tip. The physician can adjust the timing of seed firing by programming the controller/transmitter device 240. When satisfied with the local and controller/ transmitter device 240 electrograms, the catheter (or a seed delivery mechanism residing within the catheter) may be removed, and a new delivery mechanism containing the next pacing seed may be inserted and navigated to the next pacing site. Because seeds can be fired in any order, or not fired at all, a physician may deliver the seeds in any order. When the heart is deemed to be beating in synchrony, no further seeds need be implanted. Alternatively, if it has been determined that the seeds are small enough that they do not substantially impair local tissue function, then an array of seeds may be delivered to the veins and/or heart wall, and the physician can program a subset of seeds to fire in a sequence that optimizes the pumping efficiency of the heart. Ejection fraction and cardiac output may be measured to determine pumping efficiency. On any given heartbeat, some or all of the seeds would fire. The controller 240 may be programmed to sequentially fire seeds, or some seeds may fire simultaneously.

Figure 6:
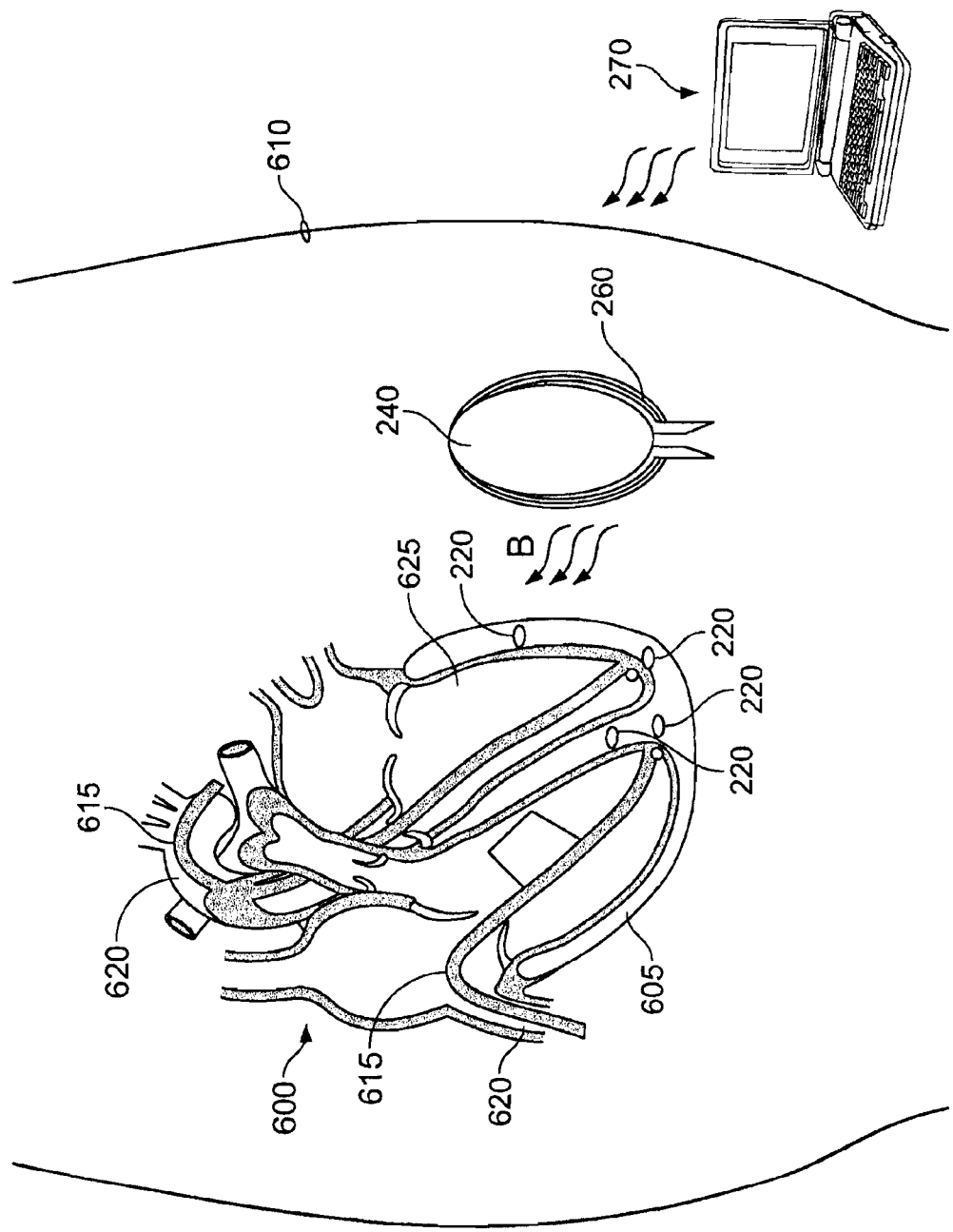
FIG. 6 is a diagram of the system shown in FIG. 2A and of an example wireless electrode assembly delivery catheter.

FIGS. 6-10 show an example of a mechanical design for a seed electrode assembly and an example seed delivery device and method. Referring first to FIG. 6, a system of the type shown in FIG. 2 is shown where three seed electrode assemblies 220 have been implanted within tissue of the heart 600, and in particular, within a myocardial wall 605 of the heart 600. In addition, the controller/transmitter device 240 is shown implanted beneath the skin 610 of the patient. The antenna 260 extends from within the controller/transmitter device 240 at one end of the device 240, and then extends around the periphery of the device 240, as described previously. The external programming device 270 is also shown, which is used to communicate with the implanted controller/ transmitter 240.

Figure 9:
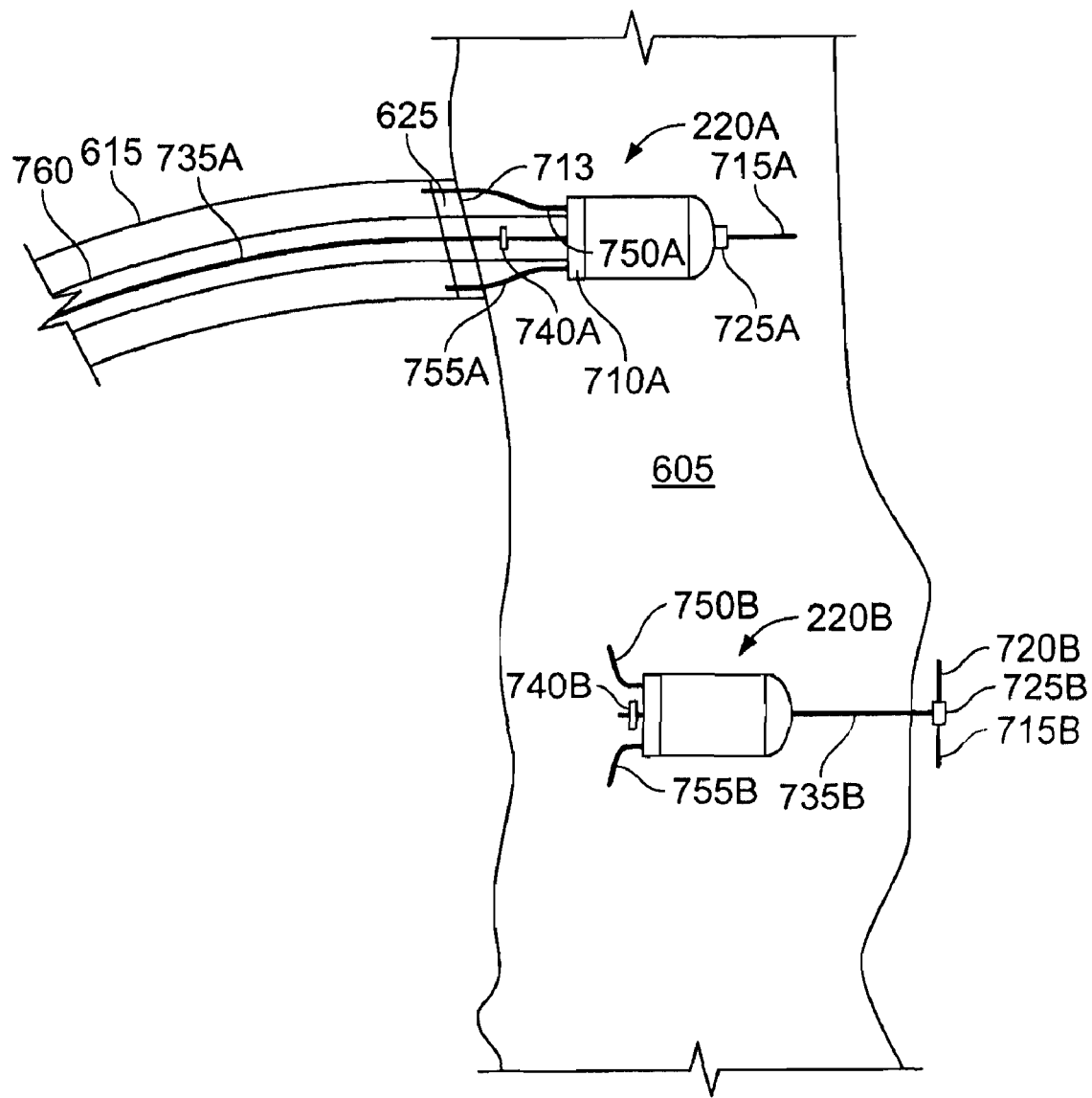
FIG. 9 is a diagram illustrating the delivery of a wireless electrode assembly from the delivery catheter and into the myocardial wall.

Distal portions of two seed delivery catheters 615 are shown in FIG. 6, each extending within a chamber of the heart 600 and to a site near where one of the seeds 220 is located. Generally, the delivery catheter 615 enables placement of a seed 220 and the ability to sense the electrical activity at the distal tip of delivery catheter 615 through catheter tip electrode 625, so that a physician can determine if the location is a good candidate location for implantation of seed 220. If the location is a good candidate, the seed 220 may be partially inserted into the tissue as shown in FIG. 9. With the seed 220 still tethered to a pull wire 735A, the seed 220 may be charged and then discharged into the tissue, while the physician observes electrograms, including the local electrogram arising from electrode 625, and perhaps an electrogram from the distal seed electrode taken through the pull wire 735A. Upon firing the seed, if the physician determines it is not in the proper location to optimize cardiac output, then the seed 220 may be removed from that site and positioned elsewhere. If it is an appropriate location, then the seed 220 has an anchoring mechanism that can be activated to implant the seed 220 permanently within the tissue so that it retains its location.

Each of the catheters 615 is shown in FIG. 6 extending into the heart 600 through a heart entry vessel 620 such as the inferior vena cava (for right chamber entry) or aortic valve (for left chamber entry). A distal portion 625 of the delivery catheter 615 includes a sensing electrode for sensing the electrical activity at a tissue site where the seed 220 may be implanted.

Figure 7:
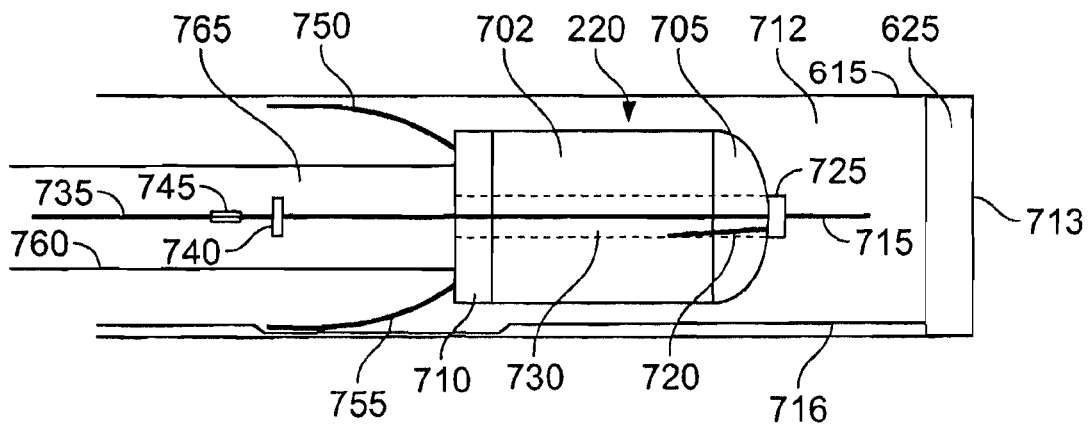
FIG. 7 is a side-view diagram of the delivery catheter shown in FIG. 6, with portions removed to show a wireless electrode assembly and additional assemblies inside the catheter.

FIG. 7 shows one of many possible embodiments of a wireless electrode assembly, or seed, 220. The seed 220 is shown in FIG. 7 within a distal portion of the seed delivery catheter 615. The seed 220 has a main body 702 that, in this example, is bullet shaped and has two bipolar electrodes 705 and 710. One of the electrodes, namely electrode 705, is located at a distal tip of the bullet-shaped seed body 702, and the other electrode 710 is located at a proximal end of the seed body 702. The bullet shape of the seed body 702 enables it to be extended into tissue such as the myocardial wall 605, as will be illustrated in later figures. In other embodiments, the "nose," or distal tip, of the seed body 702 may be more cone-shaped than the embodiment shown in FIG. 7. While the distal and proximal electrodes 705 and 710 are shown on the seed itself, other locations are possible, including placing the distal and proximal electrodes 705 and 710 at the ends of the attachment tines to achieve the maximum separation between electrodes.

The seed delivery catheter 615 consists of an elongate tube with a main lumen 712 extending though its entire length. The catheter 615 has an opening 713 at its distal end so that the seed 220 may be released from the delivery catheter 615. The catheter 615 also has the previously discussed electrode 625, which as shown extends around the periphery of the distal opening 713. An electrically conductive lead 716 is attached to the electrode 625 and extends proximally through the entire length of catheter lumen 712, or through the wall of the catheter, and outside the body (not shown in FIG. 7). The lead 716 is made of an electrically conductive material, and thus provides the local electrocardiogram (ECG) appearing at the distal electrode 625. As such, the electrical activity appearing at the location of the distal seed electrode 705 may be viewed external of the patient to determine if that is an appropriate location to implant the seed 220.

By way of example, the main lumen 712 of the seed delivery catheter 615 may have an internal diameter of about two-and-a-half millimeters, and the seed delivery catheter 615 may have an outside diameter that is slightly larger than that. In this case, the seed body 702 may have a width of about two millimeters, and the length of the seed body 702 may be about five to ten millimeters, for example. This enables the seed 220 to be implanted entirely within a myocardial wall 605, which may, for example, be about 20 millimeters thick in the left ventricle.

The seed 220 has a pair of forward-end tines 715 and 720 that each extend from a common junction point 725. Each of the tines 715 and 720 may be about three to eight millimeters in length, for example. The seed body 702 also has a central bore 730 extending longitudinally through a center of the seed body 702. In FIG. 7, which shows the seed 220 not yet implanted, one of the forward-end tines, namely tine 720, extends proximally into the bore 730, while the other forward-end tine 715 extends distally to enable it to pierce through tissue. As will be described in more detail later, the junction point 725 for the tines 715 and 720 may be pushed forward of the seed 220 body, and when the constrained tine 720 clears the central bore 730, the tines 720 and 715 are biased to snap into a lateral configuration that will be shown in a later figure. The junction point 725 is physically larger than the diameter of the central bore 730, and thus enables the seed 220 to be pulled in a proximal direction by pulling on extraction wire 735.

The seed extraction wire 735 is attached to the junction point 725, and extends proximally through the entire length of the seed central bore 730, and from there continues proximally through the delivery catheter 615 and outside the body (not shown in FIG. 7). The wire 735 may be made of an electrically conductive material so as to sense an electrical signal appearing at a distal end of the wire 735, thus serving as an extraction pull wire and as a temporary ECG lead for distal electrode 705. This is a means of sensing a bipolar electrocardiogram at a proposed implantation site before permanently implanting the seed 220, using electrode 705 (with wire lead 735) as a first electrode, and using the catheter electrode 625 and lead 716 as a second electrode.

In that the extraction wire 735 extends outside the patient's body, a physician may pull the wire 735, and given that the junction point 725 is too large to be pulled into the seed body central bore 730, pulling the wire 735 pulls the seed 220 proximally within the delivery catheter 615. The extraction wire 735 is also constructed of a material and of a diameter such that the wire 735 is rigid enough to be pushed forward to extend the junction point 725 forward of the seed 220 body and hence free the forward-end tine 720 from the constraining central bore 730. The wire 735 has stopper device 740 that is attached to the wire 735 at a point that is proximal of the seed 220 body. The stopper device 740, like the junction point 725, is larger than the seed body central bore 730, and thus constrains how far the lead junction point 725 can be extended forward of the seed body 702. The stopper device 740 is positioned on the wire 735 at a location that is far enough away from the rear-end of the seed body 702 such that wire 735 may be pushed distally far enough to free the constrained tine 720 from the seed body central bore 730.

The extraction wire 735 has a detachment mechanism 745 located on the wire 735 at a point that is immediately distal of the stopper device 740. The detachment mechanism 745 may be activated by a physician to detach the portion of wire 735 that is proximal of the detachment mechanism 745. Various detachment mechanisms may be used for the detachment mechanism 745. For example, the detachment mechanism 745 may be a high-resistance portion of a conductive line that extends proximally to a point external of the patient, and that can be heated and detached by injecting current of a specified amount into the conductive line. In this case the wire 735 may serve three purposes: extraction of a seed 220 from a location that does not provide optimal cardiac resynchronization; conduction of the tip electrode 705 ECG signal to a recorder outside the body; conduction of a burst of current to detach itself at a point 745 of relatively high electrical resistance. Another example for the detachment mechanism 745 is a mechanical configuration where the proximal detachable portion of the lead 735 may be unscrewed from the remainder of the lead 735, or where the lead 735 is pushed and turned in a certain way to effect detachment of the proximal portion from the remainder of the lead 735. A mechanical skiving or shearing means (not shown) may alternatively be applied at point 745.

The seed 220 also has a pair of tines 750 and 755 that extend from the rear end of the seed body 702. In the shown example, there are two such tines 750 and 755, though it will be understood that there may be more than two tines, or a single tine. The tines 750 and 755 assist in securing the seed 220 at a desired location within the tissue, such as within a desired location of the myocardial wall 605, to prevent the seed from migrating under the repeated stress of heart muscle contraction. The tines 750 and 755, in this example, are attached to the rear-end electrode 710 near a periphery of the electrode 710, and extend from their attachment points in a direction that is about 45 degrees from a longitudinal axis of the seed body 702. As shown in FIG. 7, however, far ends of the tines 750 and 755 are constrained by an outer wall of the catheter lumen 712, and become bent toward the longitudinal axis of the catheter 615. When the seed 220 is pushed out of the distal end of catheter 615, the tines 750 and 755 spring outwardly into their normal position (not shown in FIG. 7).

A tube 760 that is movable longitudinally within the catheter 615 is used to push the seed 220 distally within the catheter 615 and out of the catheter distal opening 713. The tube has a lumen 765 extending longitudinally through its entire length so that the wire 735 extends through the tube lumen 765. The cross-sectional diameter of the pusher tube 760 may be, for example, about half that of the catheter lumen 712. As such, where the catheter lumen 712 diameter is about 2.5 mm, the tube cross-sectional diameter may be about 1.25 mm.

Figure 8:
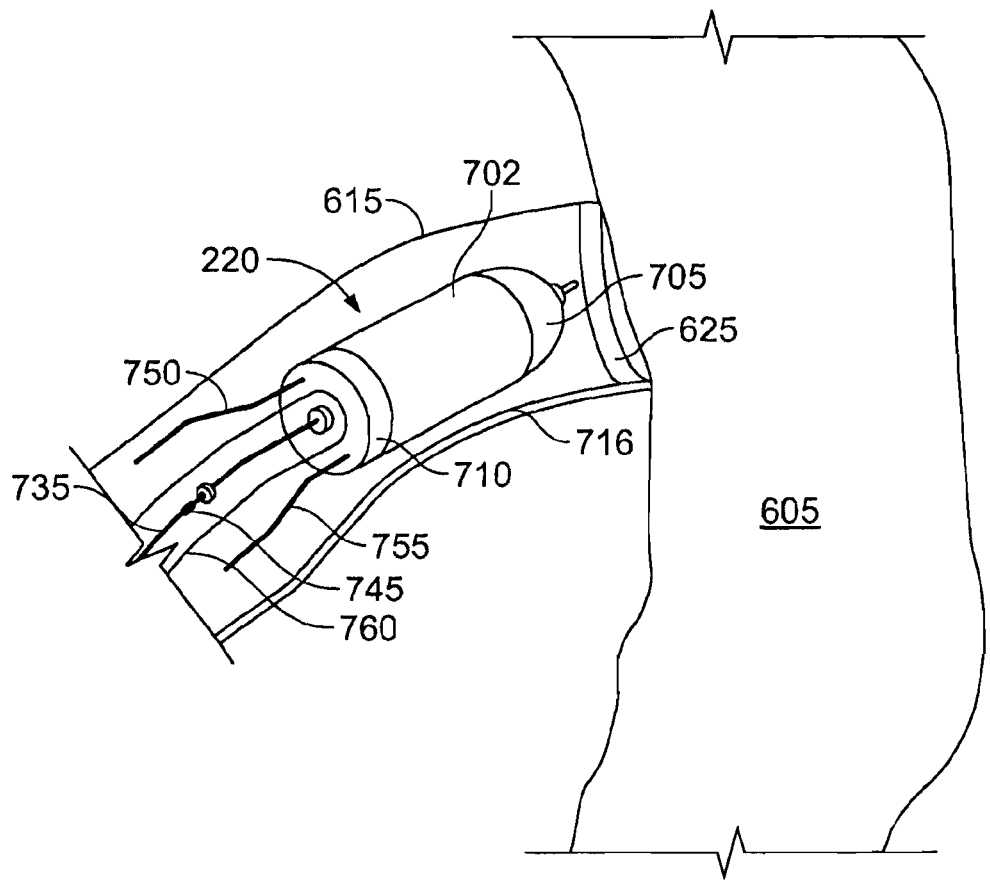
FIG. 8 is a diagram similar to FIG. 7, with a distal end of the delivery catheter pressed against a myocardial wall.

In FIG. 8, the seed delivery catheter 615, with a seed 220 contained within, is shown with its circular distal electrode 625 pressed against the myocardial wall 605. In the configuration shown, it is possible for the electrical activity occurring at that site of the myocardial wall 605 to be monitored at a proximal end of the lead 716 to determine if the site is an appropriate candidate site in which to implant the seed 220.

Turning now to FIG. 9, two seeds 220A and 220B are shown. The first seed 220A is shown during the process of implanting the seed 220A within the myocardial wall 605, with the assistance of the seed delivery catheter 615. The second seed 220B is shown as having already been permanently implanted within the myocardial wall 605.

The first seed 220A is shown as having been pushed nearly entirely within the myocardial wall 605. This was accomplished by the physician pushing the push tube 760 within the seed delivery catheter 615 so as to push the seed 220A out of the catheter's distal opening 713. The forwardly extending distal tine 715 served to pierce the myocardial wall 615 and permit implantation within the wall 615.

In the position shown in FIG. 9, the seed's rear-end tines 750A and 755A are still partially within the seed delivery catheter 615 and thus are still being constrained from extending outwardly from the seed body's longitudinal axis. As such, it is still possible for the physician to pull back the seed 220A from this position by pulling on the seed extraction wire 735A. If the seed 220A were to have been pushed a little further so that the proximal tines 750A and 755A become extended, then it may not be possible to pull back the seed 220A. As discussed previously, seed 220A may be charged and commanded to discharge while wire 735 serves as a lead to monitor the electrical activity at the forward end of the seed 220A. The physician may determine that the present positioning is not appropriate, and wire 735 may then be pulled to extract the seed, which may then be moved to an alternate location.

Also in the position shown in FIG. 9, the wire 735 has not yet been pushed forward to deploy the distal tines 715A and 720A (750A not shown in FIG. 9). Deploying the distal tines 715A and 720A is done as follows. First, the pushing tube 760 is used to push the seed 220A so that, firstly, the proximal tines 750A and 755A are freed from the delivery catheter 615 and thus extend outwardly, and secondly, the seed's distal tine junction point 725A extends distally of the seed, and preferably entirely through the myocardial wall 605. In particular, the junction point 725A and one of the forward-end tines 715 are both positioned outside the myocardial wall 605 in FIG. 9. Next, the wire 735A is pushed distally until the lead stopper device 740 becomes flush with the proximal seed electrode 710A. When this occurs, the constrained tine 720A becomes removed from the seed body central bore, thus allowing the two distal tines 715A and 720A to pop into the lateral position. Seed 220B is shown in the deployed position, the proximal tines 750B and 755B are shown extended, and the two distal tines 715B and 720B are outside the myocardial wall 605 and extend laterally from the junction point 725B.

Figure 10:
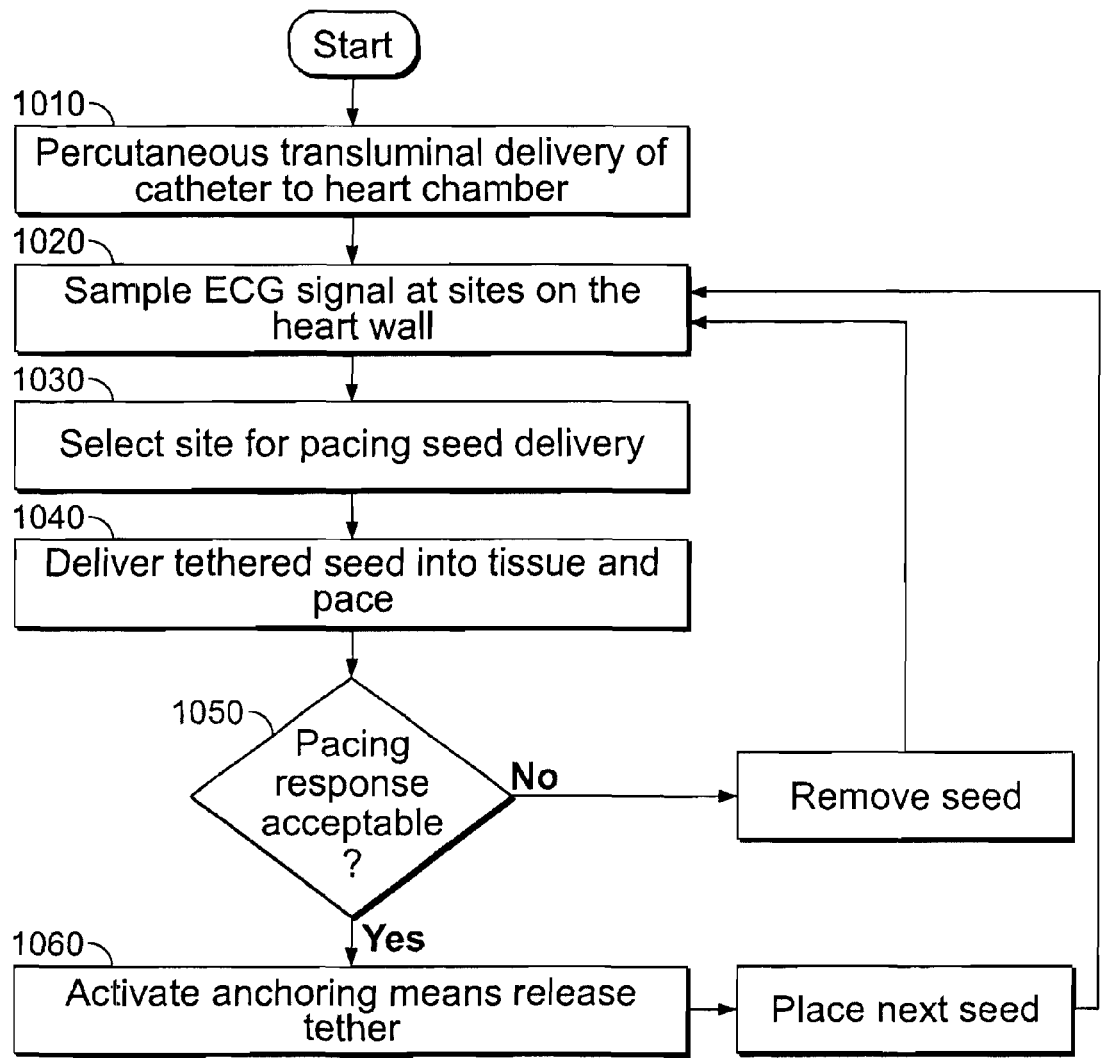
FIG. 10 is a flow chart of a method for delivering and implanting wireless electrode assemblies.

Referring now to FIG. 10, a flowchart is shown that describes a method of delivering a seed 220 using the catheter 615 or another similar delivery device. The method begins at step 1010 with the percutaneous transluminal delivery of the catheter 615 to the heart chamber. This may be accomplished in the following manner. First, an introducer is used to provide entry into, for example, the femoral vein or artery (depending on where the seed 220 is to be delivered). The catheter 615 is then inserted so that its distal end is snaked through the inferior vena cava and into the right atrium, for example. Thus, a seed 220 may be delivered in the right atrium. The distal end of the catheter 615 may also be moved from the right atrium, through the tricuspid valve, and into the right ventricle, for delivery of a seed 220 there. The distal end of the catheter may also be pushed through the fossa ovalis, accessed on the right atrial septum, for placement of seeds 220 in the left heart chambers. Alternatively, the distal end of the catheter 615 may be snaked through the femoral artery and descending aorta, through the aortic valve and into the left ventricle, and from the left ventricle may be moved through the mitral valve into the left atrium. Navigating the catheter 615 may require that the catheter 615 have some type of navigational capability such as push and pull wires commonly used with electrophysiology catheters.

Next, at step 1020, a sample ECG signal may be taken at sites on the heart inner wall. This may be done with the catheter 615 positioned as shown in FIG. 8, for example. At step 1030, the physician selects a site at which to deliver the seed 220. Then, at step 1040, the physician delivers the seed 220 into the myocardial wall tissue, such as shown with seed 220A in FIG. 9. At this point, the seed 220 is still tethered by the lead 735A so that the seed may be pulled back into the delivery catheter 615 if necessary. Further at step 1040 a test pace is performed to test the response at this site. This may be done using the programmer 270 shown in FIG. 6 to instruct the controller/transmitter device 240 to send a charging signal and then a trigger signal to the particular seed 220.

If the pacing response is found, at step 1050, to be unacceptable, then the seed 220 may be removed and the process may be performed again starting at step 1020. If, on the other hand, the pacing response is found to be acceptable, then, at step 1060, the anchoring means for the seed 220 may be activated, for example, by moving the seed 220 entirely out of the catheter 615 and freeing the proximal tines 750 and 755 from the constraints of the catheter 615 and pushing the lead 735 to release the distal tines 715 and 720. Also at step 1060, the tether to the seed 220 may be released, for example, using the detachment mechanism 745. Having completed the implantation of the seed, it is now possible at step 1070 to begin placement of the next seed 220.

As discussed previously, each of the seeds 220 may have a filter 425 (see FIG. 4) that allows passage of a signal of a particular frequency. Thus, for example, where eight seeds 220 are implanted, each of the seeds 220 may have a band pass filter 425 of a different center frequency. To make this possible, seeds 220 may be manufactured as having one of sixteen different band pass frequencies. Thus, up to sixteen seeds 220 may be implanted so that each seed is separately controllable. A code for the particular pass frequency may be labeled directly on the seed 220 itself, or alternatively, may be labeled on the packaging for the seed 220. As such, when programming the system 200 using the programmer 270, the particular band pass frequency for each seed 220 is communicated to the pacing controller 240.

Figure 11A:
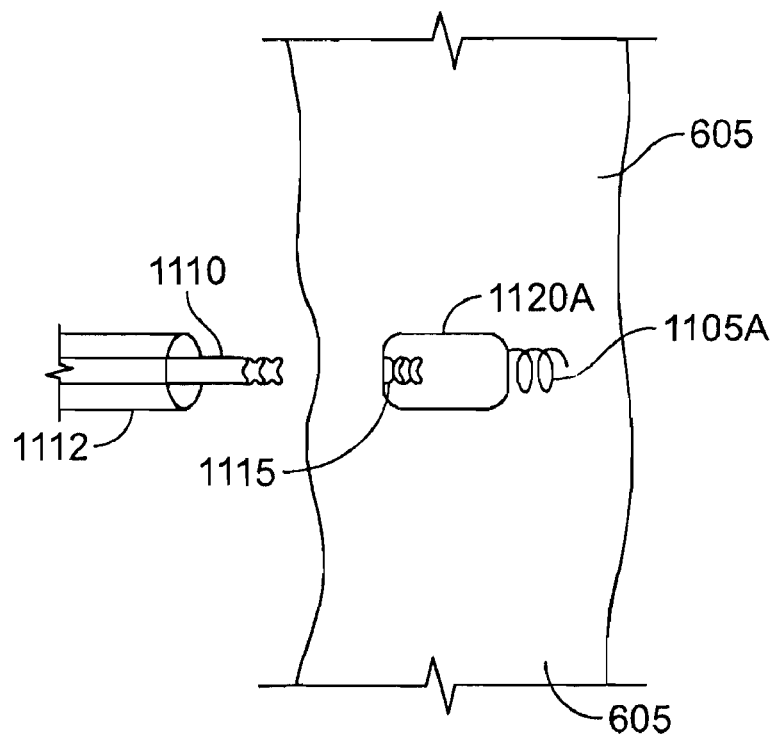
FIGS. 11A-D are diagrams of alternative embodiments of wireless electrode assemblies and associated delivery catheters, with the wireless electrode assemblies being shown being implanted within a myocardial wall.
Figure 11B:
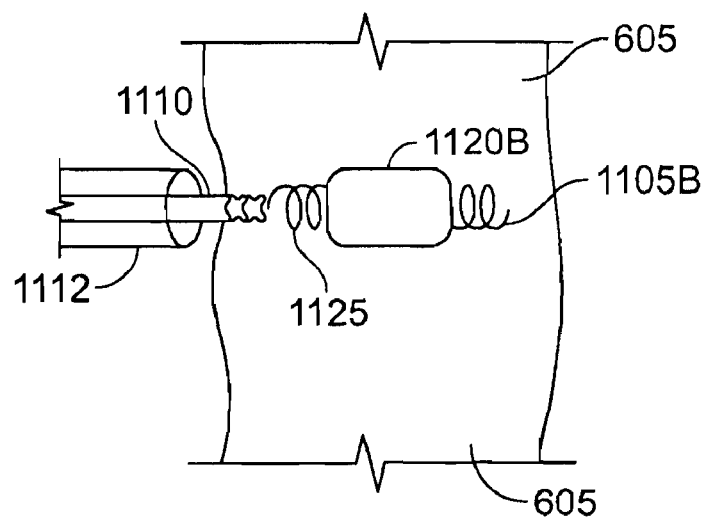
Figure 11C:
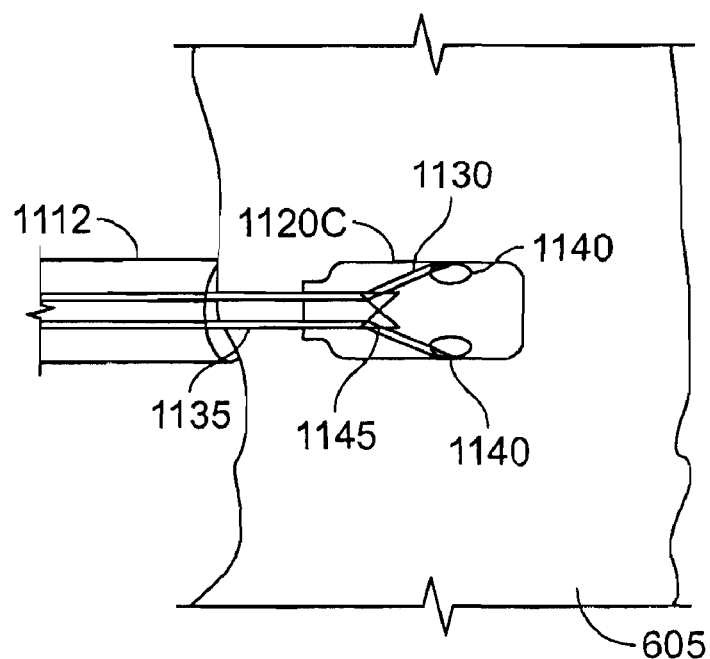
Figure 11D:
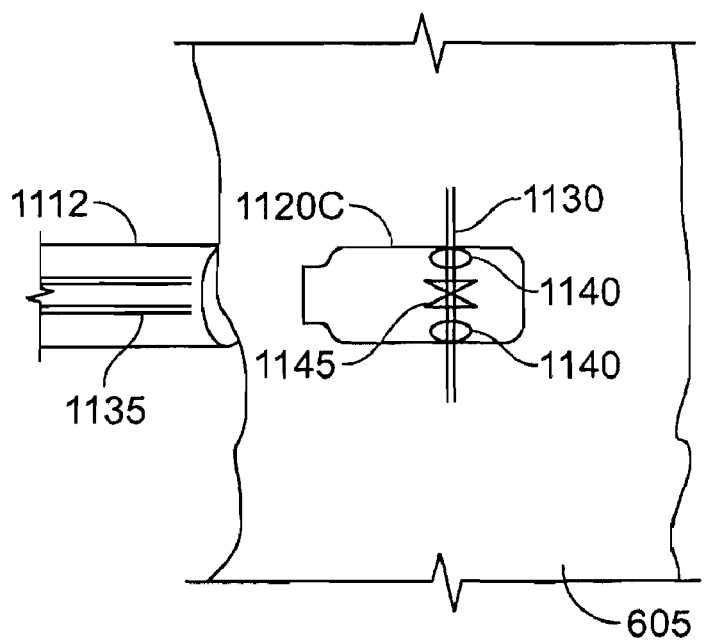

A variety of alternative embodiments are envisioned for seed delivery and detachment. For example, FIG. 11A shows a seed 1120A that is secured into the myocardium 605 with a distal spring 1105A, or "cork screw." A delivery rod 1110 provided by a delivery catheter 1112 is detached from the seed 1120A by turning the rod 1110 to engage the spring into tissue and also unscrew the threaded distal rod section 1115 from the seed 1120A. In FIG. 11B, a distal spring 1105B is screwed into the myocardium 605 using a clockwise rotation of the seed 1120B, which also unscrews the delivery rod from the seed. Upon removal of the delivery rod, proximal spring 1125 is exposed to the myocardium 605. Clockwise spring 1105B and counter-clockwise spring 1125 together prevent rotation and translation of the seed through the myocardium. A mechanism for release of the springs is not shown in the figure. A small push rod passing through the delivery rod and seed could be used to push the distal spring from the seed and into a locked position. A thin sheath could cover proximal spring 1125. The thin sheath would be retracted along with the delivery rod. Alternate means for detachment of the delivery rod include Ohmic heating of a high resistance portion of the rod, and mechanical shearing. In FIG. 11C-D, tines 1130 are pushed, using a push rod 1135 provided through the main lumen of the delivery catheter 1112, from the central portion of the seed 1120C, out through channels 1140 and into the myocardium 605, so that the tines 1130 extend laterally from the seed 1120C body (as shown in FIG. 11D), and so that the seed 1120C becomes secured within the tissue. The push rod 1135 is removable, at an attachment point, from a proximal end junction point 1145 of the tines 1130. Various mechanisms for removing, or detaching the push rod 1135 from the tine proximal end junction point 1145 may be employed, as discussed previously in connection with the FIG. 7 embodiment.

Figure 12:
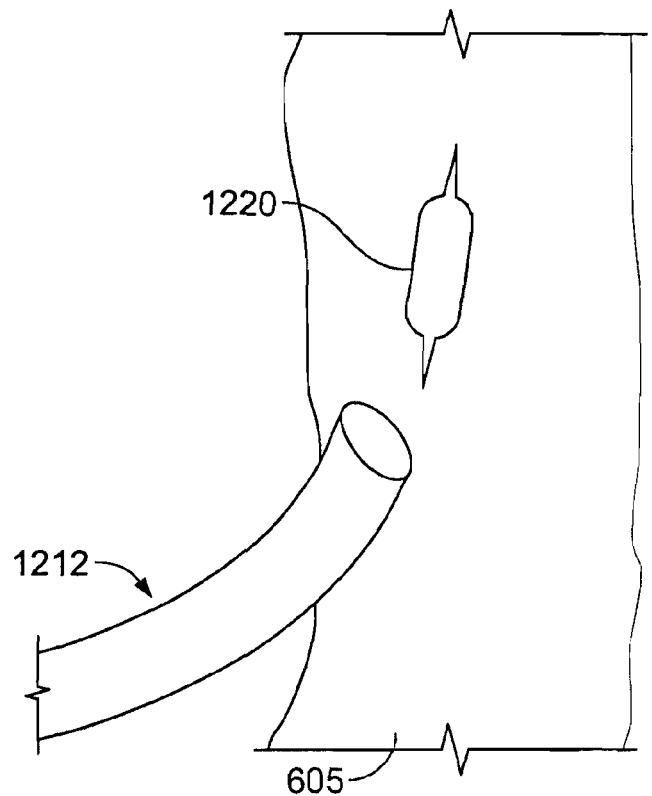
FIG. 12 is a diagram of a wireless electrode assembly and associated delivery catheter, with the wireless electrode assembly being shown implanted within a myocardial wall in a position such that its longitudinal axis is parallel with the myocardial wall.
Figure 13:
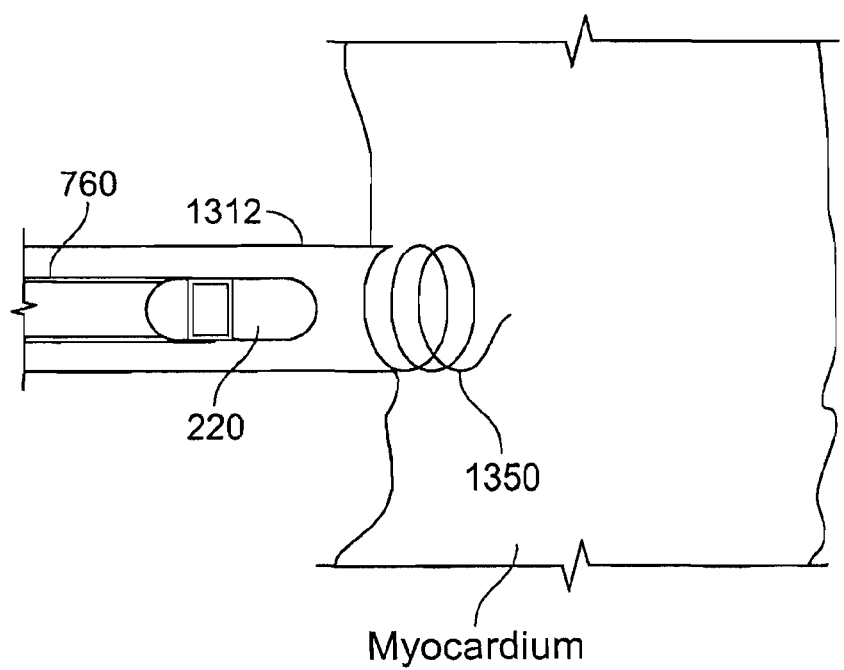
FIG. 13 is a diagram of a wireless electrode assembly and an another embodiment of an associated delivery catheter.

FIG. 12 illustrates the possibility that seeds 1220 may be placed parallel to the heart wall 605, in addition or in preference to transverse placement. This may be particularly necessary where the heart wall is thin, for example in the atria or in regions of the ventricles that contain scar tissue. Placement parallel to the wall is particularly required when the wall thickness is less than the seed length. Note that the catheter 1212 may be curved near its tip to facilitate parallel placement. Since the heart wall 605 is moving during the cardiac cycle, it may be necessary to secure the tip of the catheter 1212 to the heart tissue during seed placement. This concept is illustrated in FIG. 13, showing a cork screw 1350 temporary securement of the catheter 1312 to the wall 605. Tines that extend from the distal end of the catheter for penetration into the heart wall to secure and stabilize the catheter tip during seed delivery are also envisioned. The tines would be extended into the heart wall before seed placement, and retracted from the heart wall after seed placement.

Figure 14A:
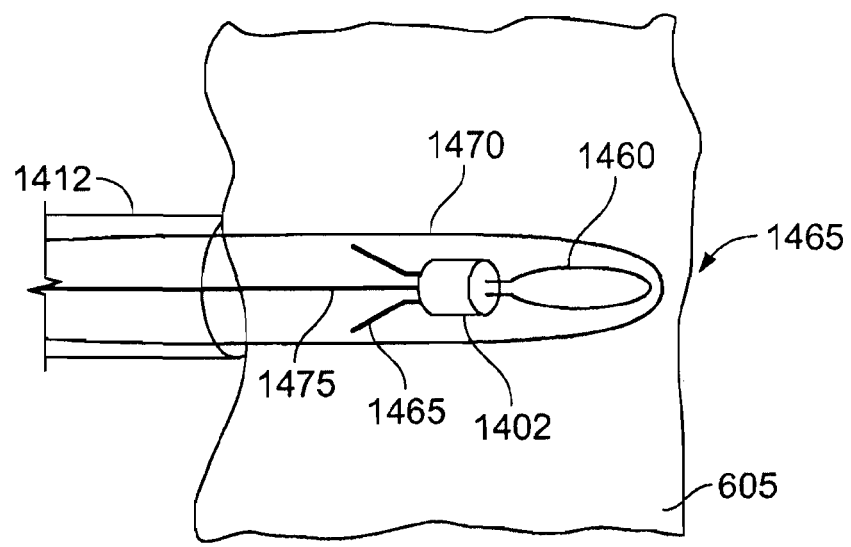
FIGS. 14A and 14B are diagrams of an alternative embodiment of a wireless electrode assembly and associated delivery catheter, with the wireless electrode assembly being shown being implanted within a myocardial wall.
Figure 14B:
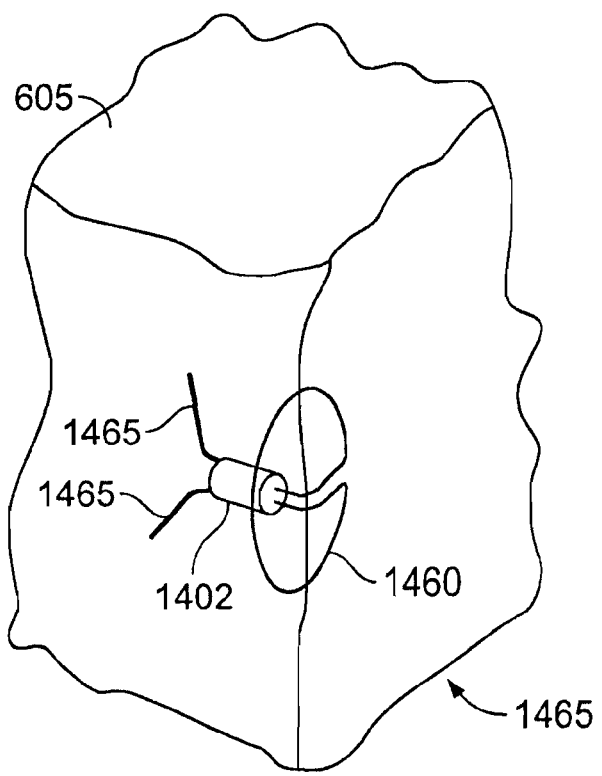

FIGS. 14A and 14B show a seed embodiment in which a seed pick-up coil 1460 also serves the function as a distal attachment, extending into the epicardial space 1465. The seed includes a seed body 1402, the distally extending coil 1460 and proximal tines 1465. The coil 1460 is wrapped down in a delivery tube 1470 provided by a catheter 1412, and expands to its full diameter after being pushed into the epicardial space 1465. The seed is pushed using a push rod, or wire, 1475 that operates to push the coil 1460 from the distal opening in the delivery tube 1470 and into the epicardial space. The seed body 1402 and proximal tines remain within the heart wall 605. The expanded coil 1460 has the advantage of collecting more magnetic flux by virtue of its larger diameter, leading to better coupling to the antenna, and a more efficient pacing system. The seed in FIGS. 14A-B can have a reduced diameter because it does not contain a relatively bulky coil. The seed body 1402 contains the capacitor and electronic components indicated in the schematic of FIG. 4. Proximal tines 1465 are shown attached to the seed for additional securement.

It is noted again, that it may be desirable to achieve maximum spacing between the proximal and distal electrodes to ensure conduction through the maximum volume of refractory tissue. For example, it may be possible for the bullet shaped seed of FIG. 4 to become encapsulated in fibrous, non-refractory tissue. In this case, the current density in tissue surrounding the fibrous capsule may be too low to cause depolarization. A solution to this problem is to use the furthest extremities of the seed as electrodes. For example, tines 715, 720, 750 and 755 (see FIG. 7) may be plated with a suitable conductive material to serve as electrodes that extend into the epicardial space. Current passing between the distal tines and the proximal seed electrode would then pass through refractory tissues. As a further precaution, the proximal tines 750 and 755 could be plated with a conductive material and serve as an extension of proximal electrode 710. Current passing between distal and proximal tines would encounter refractory tissues with a high degree of probability. Similarly, the epicardial coil 1460 of FIG. 14 may contain a central conducting coil surrounded by an electrical insulator, which is in turn coated with a conductive electrode material.

Figure 15:
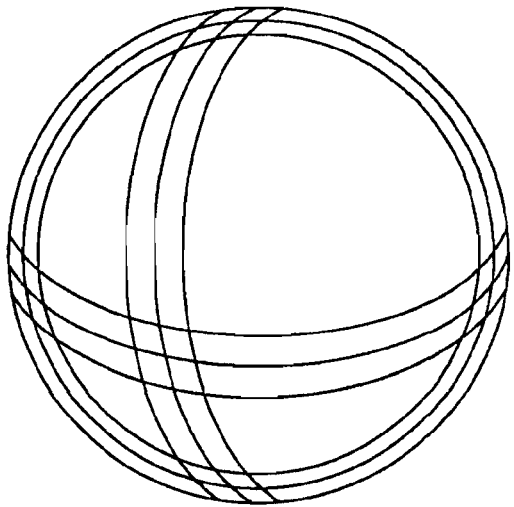
FIG. 15 is a diagram of an alternative embodiment of a coil for a wireless electrode assembly in which three orthogonal coils are wound on a single substrate.

For completeness, shown in FIG. 15 is an alternative seed coil embodiment in which three orthogonal coils are wound on a single substrate. The substrate may be made from a permeable material. Currents induced in each of the three coils would be rectified, and passed to a single capacitor. In this embodiment, the orientation of the seed relative to the transmit antenna is immaterial. This is important because there is no coupling between a coil having its axis parallel to the plane of the antenna, and it may not always be possible to implant a seed with its axis perpendicular to the plane of the antenna. The seed of FIG. 15 collects magnetic flux in each of three orthogonal directions, so that maximum flux is collected independent of the orientation of the incident magnetic field.

The electrical parameters in the seed circuit of FIG. 4, and the geometry of the antenna 260 of FIG. 6 may be optimized by the use of a computer model for the response of the seed to the magnetic field generated by the antenna. The fundamental requirement is that the energy stored on capacitor 405 of FIG. 4 after charging is complete be equal to the pacing threshold energy for the tissue surrounding the seed. For example, conventional pacemaker electrodes deliver on the order of four micro-Joules ($E_0=4$ µJ) of energy to pace the tissue each time the heart beats. This number depends upon the tissue type, pulse shape, and electrode geometry, but will be used here as an example. The total energy required to pace N sites is then on the order of N times the threshold energy $E_0$. For example, if ten sites are paced using ten seeds, then the total energy requirement will be on the order of $NE_0=40$ μJ for every heart beat. The energy that must be supplied by the antenna 260 on each heartbeat is this minimum pacing energy times the overall efficiency of coupling energy from the antenna to seeds.

The energy delivered to each seed in a charging time, τ, may be computed for a given set of seed circuit parameters and a measured or computed magnetic field versus time at the site of the seed in question. This is possible because the voltage induced in coil 410 is known to be equal to the time rate of change of magnetic flux linking the coil. The steps needed to compute the energy stored on a given seed capacitor are:

For a given antenna shape, location and orientation, and antenna current waveform, I(t):

1) Compute the magnetic flux linking a seed coil 410 at a given location and a given orientation relative to the antenna, residing in a tissue medium having realistic frequency dependent values of electrical conductivity and permittivity.

2) Compute voltage induced in the coil (and modeled as a voltage in series with the coil 410) as the time rate of change of the flux computed in step 1).

3) With the switch 418 in position 1, use seed circuit equations to compute the charge on capacitor 405 versus time, and therefore the energy stored on the capacitor (equal to square of charge divided by two times the capacitance of 405).

Generally speaking, the magnetic field falls off rapidly as the separation between the seed and the antenna increases. While this may not be true for very large antennas, the body dimensions limit the practical dimensions of the antenna. The exact location (and orientation if the seed does not have a tri-axial coil) of the seed will determine the antenna current magnitude and ON-time required to charge that seed. The seed that links the least magnetic flux from the antenna will then determine these antenna parameters, since all seeds must be capable of acquiring the threshold energy for pacing. We may refer to this seed as the "weakest link", and it alone will be used to compute optimal antenna current waveform and coupling efficiency.

The energy coupling efficiency is defined as the ratio of the total energy delivered to the seed capacitors, NEO, divided by the sum of all energy lost by the antenna during the on-time. Antenna losses that may be included in simulations include:

Energy delivered to all seeds=$NE_0$
Power dissipated (as Ohmic heat) in seed circuit during charging
Power dissipated (as Ohmic heat) in antenna circuit during charging
Power dissipated (as Ohmic heat) by eddy currents induced in conductive body tissues The energy coupling efficiency is then given by $NE_0$ divided by the sum of losses listed above over the duration of the charging time. The Ohmic heat in the antenna circuit is primarily due to $I^2R$ losses in the antenna itself, and hysteresis losses in any magnetic materials that may be included in the antenna design. This statement is also true for Ohmic heating in the seed circuit. Once the parameters of the antenna current waveform needed to charge the weakest link seed to the pacing threshold energy have been determined, these losses may be computed. Once the antenna current waveform parameters have been determined, the electric field, E, generated at any point in the body may be computed. Then, given a knowledge of the electrical conductivity of all body parts affected by the antenna, the current density may be computed at any point in the body as $J=\sigma E$, where σ is the electrical conductivity at that point. The Ohmic heating due to eddy currents is then found by integrating the power loss density $J \cdot E = \sigma |E|^2$ over the volume of the patient's body. Since both the magnetic field and the electric field produced by the antenna waveform at any point in space may be derived from the magnetic vector potential, the following further steps may be used to compute coupling efficiency:

4) Compute the vector potential, A, arising from a given current waveform in the seed medium, using realistic tissue conductivity and permittivity.
5) Compute the magnetic field at the site of the seeds as B=curl(A)
6) From 5) determine antenna current waveform parameters needed to charge the weakest link seed to the pacing threshold energy
7) Compute antenna circuit losses for the current waveform found in 6)
8) Compute the sum of all seed circuit losses given a set of seed locations and orientations to the field, and the field computed in 5) using 6)
9) Compute the electric field at points in space as $E=-\partial A/\partial t$
10) Integrate $\sigma |E|^2$ over the patient's body using known or estimated values for the electrical conductivity a at each point in space to determine energy lost to absorption by body tissues
11) Compute efficiency as charging energy delivered to seeds divided by the charging energy plus the losses computed in 7)-10)

Optimization of seed design, antenna design, and antenna circuit waveform is performed by iterating steps 1)-11) to maximize coupling efficiency. The lifetime of the transmitter battery is readily computed from the energy coupling efficiency since on each heart beat the antenna must supply the total pacing energy, $NE_0$ divided by the coupling efficiency. The total energy contained in the battery is its volume times its energy density. The total expected number of heartbeats that the system can pace is then the total battery energy times the energy coupling efficiency divided by the pacing energy per heartbeat, $NE_0$. Making an assumption about the average heart rate, say 72 beats per minute, then yields the battery lifetime in minutes.

In one example calculation a seed contained a coil 3 mm long by 2 mm diameter wound on a core with relative permeability equal to ten. The capacitance was chosen to make the coil resonant at the frequency of the applied magnetic field. A further constraint was made by choosing the Q of the coil (resonant frequency divided by the width of the resonance peak) equal to ten. This constraint of a modest Q provides a margin for possible frequency dispersion by conductive tissues, and a manufacturing margin. Given these assumptions it was found that a magnetic field directed along the axis of the coil must have a magnitude of about 0.001 Tesla (1 mT) to provide the minimum pacing energy of 4 μJ. The antenna model in this calculation was a five inch diameter circular loop of copper having a total weight of 100 grams. The tissue model employed was a combination of heart muscle and blood, having about the same electrical conductivity. When the weakest link seed was placed at a distance of three inches from the plane of the antenna, the following was determined: The optimal energy coupling occurred at a frequency of about 30,000 Hz (30 kHz), where efficiency peaked at about 0.5%, and the lifetime of a 100 gram battery with 720 Joules/gram energy density was about 2 months.

The efficiency can be improved by improving magnetic coupling between the seeds and the antenna. This may be accomplished by using multiple antennas, for example one loop on the ribs over the anterior side of the heart, and one loop on the ribs over the posterior side of the heart. Two or more antenna loops may insure that the weakest link seed is closer to a loop than the three inches used in the example above. An alternative location for an antenna loop may be a loop inserted into the right ventricle of the heart, and attached to a controller placed at the usual pectoral implant location. Such a loop would be located closer to all seeds, particularly since the antenna is energized during systole when the heart is contracted.

Battery lifetime can be extended indefinitely by employing a rechargeable battery. The battery may receive energy for recharging by inductive coupling to antenna 260. External antennae and transmitters for recharging could be located under or around the patient's bed or chair, or be integrated into special clothing. As an alternative to a rechargeable battery, the antenna, transmitter, and battery of FIG. 3 could be integrated into clothing or a disposable patch worn by the patient. ECG signals needed to time the seed pacing could be received via an inductive link from a conventional pacemaker with right atrial and right ventricle leads. In this case, elaborate antenna designs could be incorporated into the special clothing. For example, the antenna could have a portion that surrounds the chest at the latitude of the heart.

Figure 16:
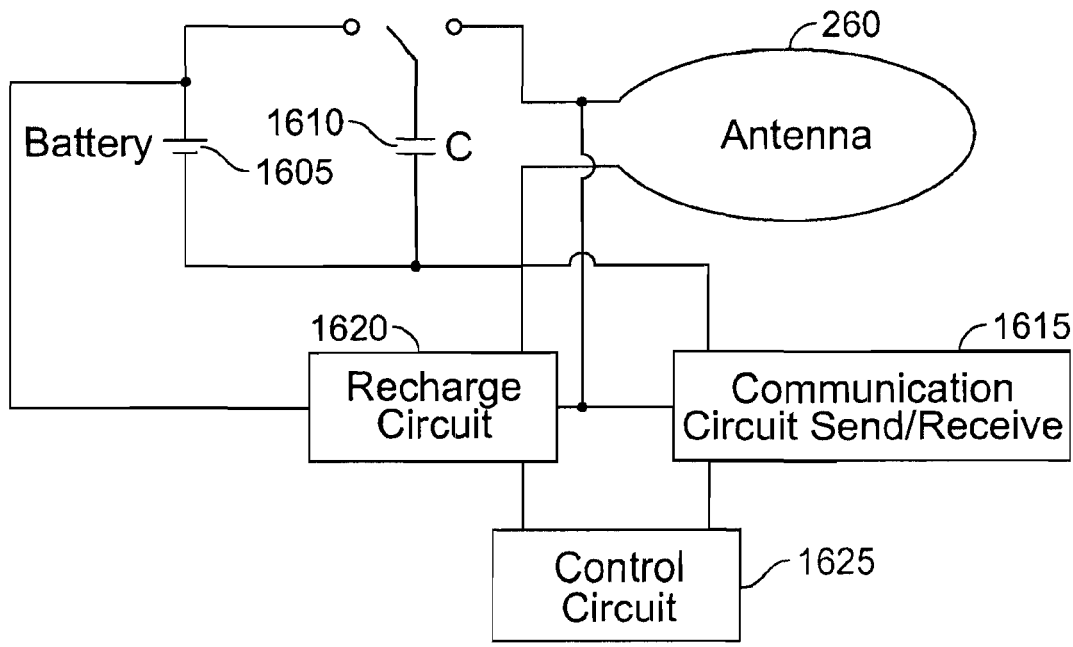
FIG. 16 is a part schematic and part block diagram of a circuit that may be included within embodiments of wireless electrode assemblies to enable them to receive and to transmit information.
Figure 17:
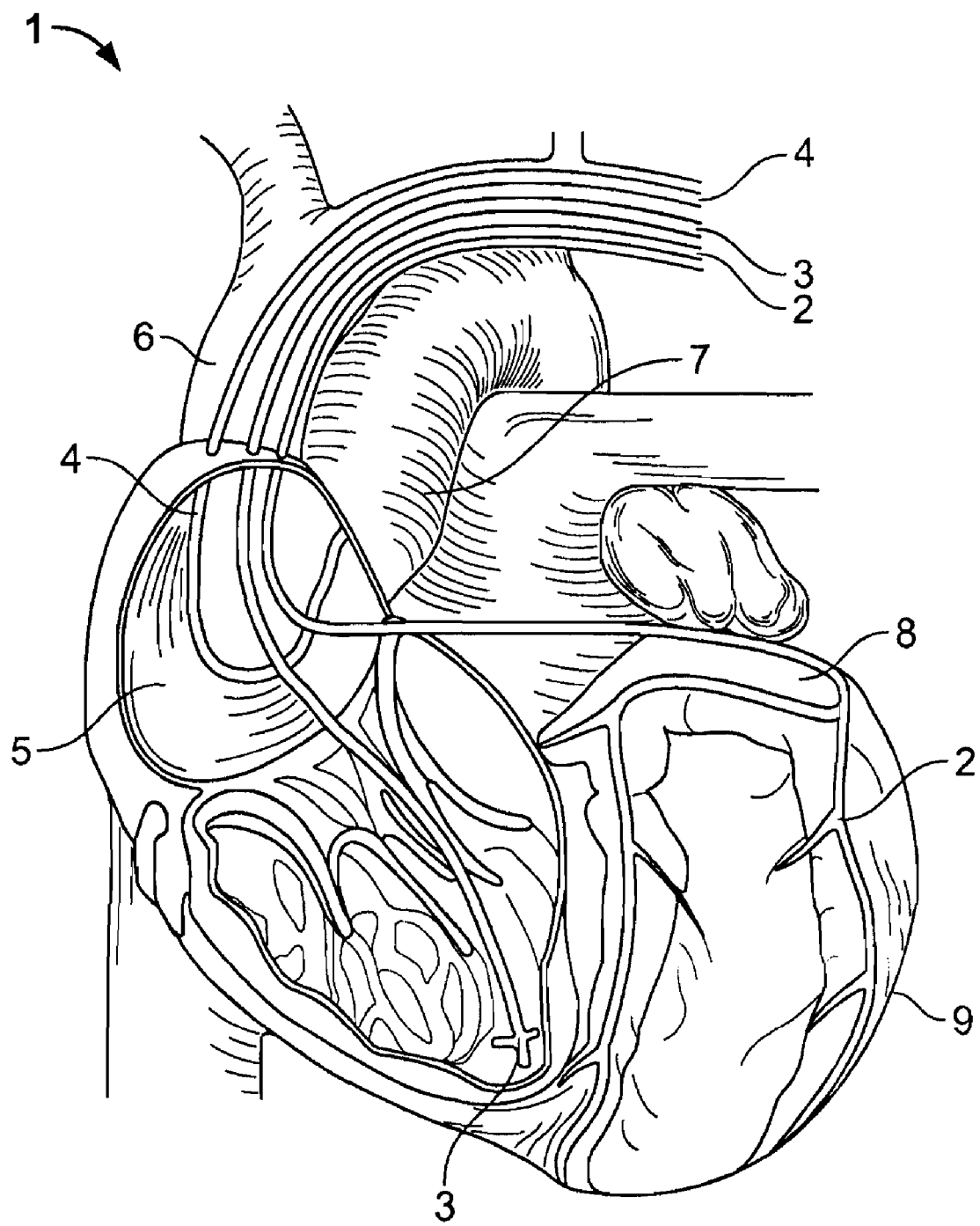
FIG. 17 is an example of a prior art, three-lead pacing system, showing one lead placed in a vein over the left ventricle.

FIG. 16 shows a schematic diagram of an antenna 260 with the charging current waveform being supplied by capacitive discharge through the antenna 260, and capacitor recharge provided by a battery 1605. The value chosen for the capacitor 1610 determines if the current waveform has a single peak or whether the current rings down in a damped sine waveform. Communications electronics 1615 sends pacing discharge signals to the seeds, but may also receive ECG signals from the seeds or a conventional pacemaker. The charge electronics 1620 receives energy via the antenna from an inductive link to an external antenna, to recharge the battery. A control circuit 1625 controls the operation of the recharge circuit 1620 and the communications electronics 1615.

It should also be noted that the seed circuit of FIG. 4 can be simplified by omission of the capacitor and voltage controlled switch. That is, the seed circuit may consist simply of a coil connected across electrodes in contact with tissue. In this case a magnetic field pulse induces a voltage pulse in the seed coil, and the induced voltage directly discharges into tissue. If all seeds are the same, pacing of all seeds is simultaneous. However, the rise time of the induced voltage can be adjusted by adjustment of the coil parameter number of turns, core permeability, and adjustment of a resistor in series with the coil. Thus, a collection of seeds having varying rise times can be used to synchronize the firing sequence of the seeds. The controller may sense a singe local ECG, for example the atrial or right ventricle electrode of a special transmitting seed or of a conventional pacemaker that transmits data to the controller. A burst of current into the antenna would then fire all seeds, with the precise time of firing determined by the electrical properties of each implanted seed.

It is also noted that alternative sources of power for the seeds may be envisioned. For example, the mechanical energy of the beating heart is many orders of magnitude larger than the energy required to pace the seeds. At the site of a seed, the heart muscle thickens during systole and thins during diastole as the heart beats. It is estimated that a one mm diameter transducer placed across the heart muscle could generate 65 μJ of energy due to the contraction of the heart, more than ten times the energy needed to pace. A simple mechanical to electrical transducer having nominal efficiency could provide the energy to pace a seed. Other miniature local sources of energy have been suggested in recent literature. These include: piezoelectric and electro-active polymer materials that transduce mechanical to electrical energy; bio-batteries that convert body heat and/or blood flow energy to electrical energy; and tiny amounts of radioactive material that emit short range alpha or beta particles that are readily shielded.

A number of embodiments of the invention have been described. Nevertheless, it will be understood that various modifications may be made without departing from the spirit and scope of the invention.

What is claimed is:

1. A body implantable wireless electrode assembly comprising:
    a charge storage device operatively coupled to discharge stored charge across a pair of electrodes that are positionable to be in contact with myocardial tissue;
    a receiver coil that inductively couples an externally provided charging signal to charge the charge storage device and that receives externally provided wireless control signals;
    control circuitry that triggers the discharge of stored charge from the charge storage device upon receipt of a wireless control signal that indicates that a storage capacitor is to be discharged and that includes information that identifies the body implantable electrode assembly from among other such body implantable electrode assemblies;
    a mechanism configured to secure the wireless electrode assembly entirely within myocardial tissue within a heart; and
    wherein the wireless electrode assembly is sized, shaped, and positionable: (1) for delivery to the interior of the heart via an intravascular route, and (2) for implant entirely within the myocardial tissue of the heart wall.

2. The electrode assembly of claim 1 wherein the electrode assembly is tuned to respond to a particular frequency of wireless control signal.

3. The electrode assembly of claim 2 wherein the electrode assembly has a filter that filters all but a selected frequency.

4. The electrode assembly of claim 1 wherein the mechanism that secures the assembly entirely within the myocardial tissue includes one or more tines.

5. The electrode assembly of claim 4, wherein at least one of the tines is configured to controllably extend from within a housing of the wireless electrode assembly into the surrounding tissue.

6. The electrode assembly of claim 5, wherein at least one of the tines is configured to extend radially outward from the wireless electrode assembly in response to actuation by an intravascularly-deliverable elongate member coupled to the wireless electrode assembly.

7. The electrode assembly of claim 1 wherein the electrode assembly does not include an internally generated power source.

8. A method of controlling the delivery of electrical signals from a plurality of wireless electrode assemblies that each have a pair of electrodes that are in contact with myocardial tissue, wherein each of the electrode assemblies may be charged by inductive coupling and subsequently discharged to deliver electrical energy across the pair of electrodes in contact with myocardial tissue, wherein each electrode assembly includes a mechanism configured to secure the electrode assembly entirely within myocardial tissue within a heart, and wherein the wireless electrode assembly is sized, shaped, and positionable: (1) for delivery to the interior of the heart via an intravascular route, and (2) for implant entirely within the myocardial tissue of the heart wall, the method comprising:
- wirelessly transmitting a charging signal that is received by each of the plurality of the wireless electrode assemblies to charge a respective storage capacitor of each of the plurality of wireless electrode assemblies at the same time; and
- wirelessly transmitting control signals that are received by the wireless electrode assemblies to trigger the discharge of the storage capacitor in a selected one of the wireless electrode assemblies.

9. The method of claim 8 wherein the wirelessly transmitted control signals are transmitted at different frequencies, wherein one of the different frequencies identifies the selected one of the wireless electrode assemblies.

10. The method of claim 8, comprising securing the wireless electrode assembly entirely within myocardial tissue using one or more tines.

11. The method of claim 10, wherein the securing the wireless electrode assembly includes controllably extending at least one of the tines from within a housing of the wireless electrode assembly into the surrounding tissue.

12. The method of claim 11, wherein the securing the wireless electrode assembly includes extending at least one of the tines radially outward from the wireless electrode assembly in response to actuation by an intravascularly-deliverable elongate member coupled to the wireless electrode assembly.

13. A wireless electrode assembly, comprising:
- a charge storage device configured to discharge stored charge across a pair of electrodes that are positionable to be in contact with myocardial tissue;
- a receiver coil configured to inductively couples an externally provided charging signal to charge the charge storage device and that receives externally provided wireless control signals;
- control circuitry configured to trigger the discharge of stored charge from the charge storage device in response to a wireless control signal including information that identifies the wireless electrode assembly from among other such wireless electrode assemblies;
- a mechanism including one or more tines configured to secure the wireless electrode assembly entirely within myocardial tissue within a heart;
- wherein the wireless electrode assembly is sized, shaped, and positionable: (1) for delivery to the interior of the heart via an intravascular route, and (2) for implant entirely within the myocardial tissue of the heart wall; and
- wherein at least one of the tines is configured to extend radially outward from within a housing of the wireless electrode assembly in response to actuation by an intravascularly-deliverable elongate member coupled to the wireless electrode assembly.

* * * * *